US012788608B2

(12) United States Patent
Price et al.

(10) Patent No.: US 12,788,608 B2
(45) Date of Patent: Nov. 10, 2026

(54) FRONTAL SUPPORTIVE ORTHOSIS

(71) Applicant: Aspen Medical Products, LLC, Irvine, CA (US)

(72) Inventors: Jane Price, Anaheim, CA (US); Geoffrey Wong, Costa Mesa, CA (US); Albert V. Romo, Lakewood, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 0 days.

(21) Appl. No.: 19/393,312

(22) Filed: Nov. 18, 2025

(65) Prior Publication Data

US 2026/0137544 A1 May 21, 2026

Related U.S. Application Data

(60) Provisional application No. 63/722,439, filed on Nov. 19, 2024.

(51) Int. Cl.

*A61F 5/03* (2006.01)
*A61F 5/02* (2006.01)
*A61F 7/02* (2006.01)
*A61F 7/00* (2006.01)

(52) U.S. Cl.

CPC ................ *A61F 5/028* (2013.01); *A61F 5/02* (2013.01); *A61F 7/02* (2013.01); *A61F 2007/0027* (2013.01); *A61F 2007/023* (2013.01)

(58) Field of Classification Search

CPC .... A61F 5/028; A61F 5/02; A61F 7/02; A61F 2007/023; A61F 5/03; A61F 5/026; A61F 5/024; A61F 5/022

See application file for complete search history.

(56) References Cited

U.S. PATENT DOCUMENTS 3,927,665 A * 12/1975 Wax ........................ A61F 5/028
602/19

* cited by examiner

*Primary Examiner* — Camtu T Nguyen
(74) *Attorney, Agent, or Firm* — Rutan & Tucker, LLP

(57) ABSTRACT

The disclosure provides an orthotic brace including a tightening mechanism including a pair of belt pulley bases, a pair of strap pulley bases, a pair of cord segments, and elastic strapping, where each belt pulley base is connected to one of the pair of strap pulley bases via a cord segment, and where the elastic strapping elastically couples the pair of strap pulley bases together. Additionally, the orthotic brace includes a pair of belt arms, wherein each belt arm is configured to couple to one of the pair of belt pulley bases and extend outwardly from the tightening mechanism. The disclosure still further provides an orthotic brace that includes a pair of tightening straps, wherein each tightening strap is configured to couple with a distal end of a respective one of the pair of belt arms and further configured to couple with the tightening mechanism.

20 Claims, 33 Drawing Sheets

FIG. 1C1
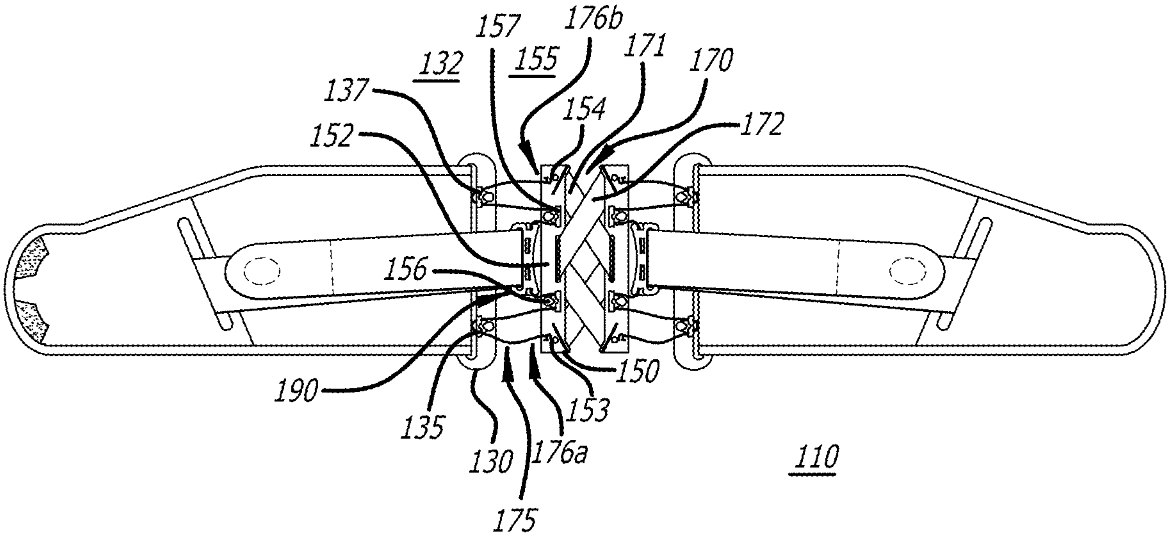
FIG. 1C2
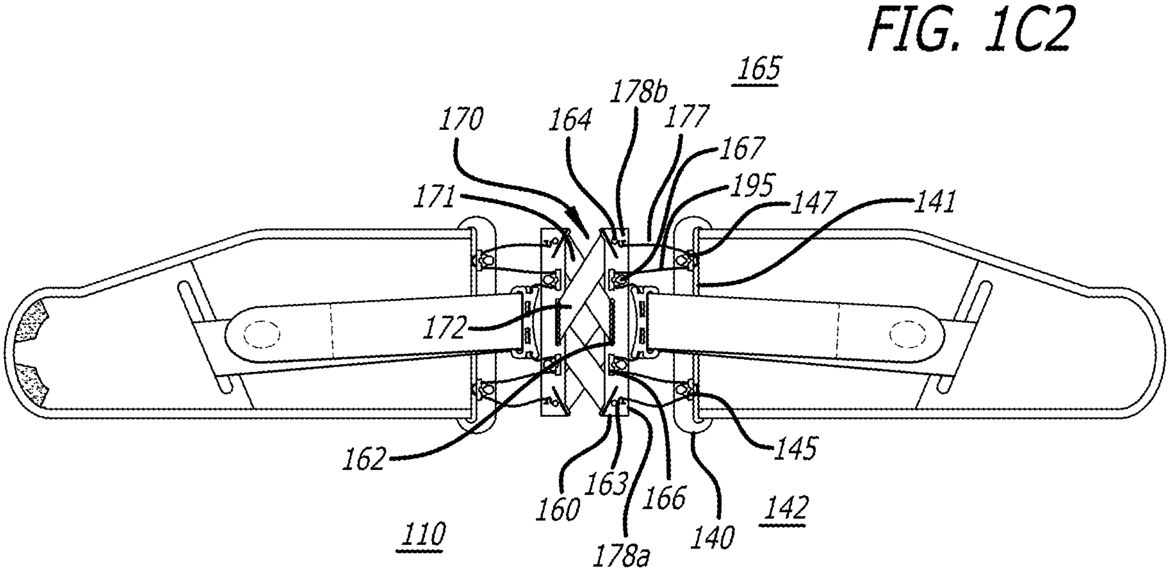

FRONTAL SUPPORTIVE ORTHOSIS

CROSS-REFERENCE TO RELATED APPLICATIONS

This application claims priority to U.S. Provisional Patent Application No. 63/722,439, filed Nov. 19, 2024, entitled "Frontal Supportive Orthosis," which is incorporated by reference in its entirety into this application.

FIELD

Embodiments of the disclosure relate to the field of medical devices. More specifically, one embodiment of the disclosure relates to an orthopedic brace and components thereof.

BACKGROUND

The following description includes information that may be useful in understanding the described invention. It is not an admission that any of the information provided herein is prior art or relevant to the presently claimed invention, or that any publication specifically or implicitly referenced is prior art.

Orthopedic braces usually need to be adjusted or customized in some manner to conform to the body part(s) of the wearer being braced, and then properly positioned. One type of orthopedic brace is referred to as a "lumbar-sacral orthosis" or by the acronym "LSO." A typical LSO commonly has at least two portions, a rigid portion that provides compression against and support to a lower back (sacrum) region of the wearer, and a flexible belt arms securing the orthopedic brace to the body.

While capable of providing adequate support for wearers (patients) with a slim or average physique, conventional LSOs have failed to provide adequate support to pregnant patients or bariatric patients. More specifically, the flexible belt arms are based on soft goods, namely a first flexible, belt arm with a hook and loop fastener placed on an outer side of the first belt arm to be affixed to a complementary hook and loop fastener located on a top (anterior) surface of a second flexible belt arm. These belt arms are not designed to provide additional upward forces (lift) to support the abdominal area of the patient while, at the same time, providing sufficient compression against the lower back region of the wearer.

Additionally, for maternity and/or bariatric patient, the donning process for conventional LSOs is quite challenging, especially when trying to ensure that the LSO properly fits under her or his abdominal region to support an extended abdominal region while, at the same time, supporting the lower back region of the patient to achieve relief.

BRIEF DESCRIPTION OF THE DRAWINGS

Illustrative examples are described in detail below with reference to the following figures:

FIG. 1C1-1C2 are posterior views of the first embodiment of FIGS. 1A-1B without the padded posterior sleeve 105 thereby illustrating a first embodiment of the tightening mechanism 110 according to an implementation of the disclosure;

FIG. 1C3 is an illustration of the directions each of the belt pulley bases 130, 140 and the strap pulley bases 150, 160 move in response to the tightening of the brace 100 when the tightening straps 180, 185 are pulled outwardly according to an implementation of the disclosure;

FIG. 3 is a detailed posterior view of a portion of the tightening mechanism 110 illustrating an alignment of the first tightening strap fastener 190 and first and second pulleys 156 and 157 according to an implementation of the disclosure;

DETAILED DESCRIPTION

Figure 1A:
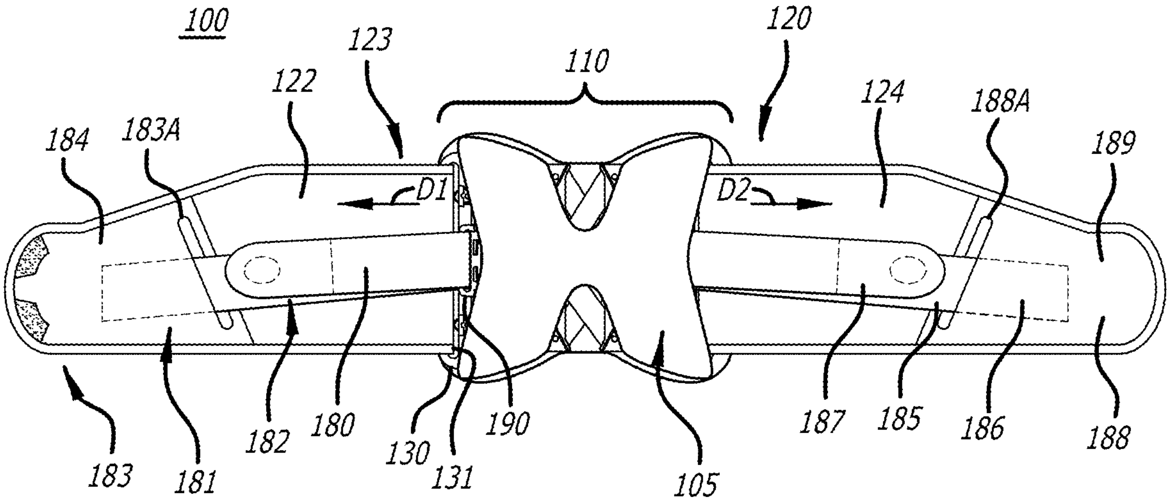
FIG. 1A is a posterior view of a first embodiment of a brace 100 worn to provide compression against a posterior region of the wearer and provide lifting forces for an abdomen area of the wear, which may be used for maternity or bariatric application according to an implementation of the disclosure.

Embodiments of the disclosure relate to a brace that, when worn, provides concurrent forces inclusive of both (i) "lifting" forces under an extended abdomen (belly) for a pregnant or bariatric patient through distal ends of the belt arms 122/124 and dual (e.g., Y-shaped) connection points of the tightening straps 180/185 in the pockets 183/188 of the belt arms, and (ii) compression in the back through the tightening mechanism 110, and specifically addressing the interaction of (i)-(ii) together. However, while the dual connection point configuration is described below, it is contemplated that a distal end of the tightening straps 180/185 may be attached to the belt arms 122/124 in accordance with any attachment scheme and/or to any type of strap anchoring member within or outside the pockets 183/188. Likewise, the proximal end of the tightening straps 180/185 may be attached to and operate in conjunction with the tightening mechanism 110, whether through the use of the strap tightening fasteners 190/195 as describe below or even attachment to the cord segments 175/177. A brace configuration that, when in operation, is adapted to concurrently provide both "lifting" forces under an extended abdomen and compression to a lower back of the wearer is contemplated with the below-described embodiments.

According to one embodiment of the disclosure, the brace includes a tightening system that interacts with a pair of tightening strap fasteners 190/195 to allow for greater flexibility during a brace tightening phase. Each of the tightening strap fasteners 190/195 is adapted with both a slot to receive its assigned tightening strap and one or more segments forming a lumen through which a segment of the cord is inserted (threaded) so that movement of the tightening strap fasteners 190/195 causes movement of sets of pulleys (mounted on a pairing of strap and belt pulley bases 130/150 or 140/160) forcing elongation of the elastic strapping 170 coupled to an outer or inner surface of laterally movable strap pulley bases 150/160, which serves to provide an elastic coupling of the strap pulley bases 150/160. An elastic coupling may be understood as providing a flexible connection between two components via an elastic element (such as a strap, band, or insert) to transmit motion or force while allowing limited relative movement.

In some embodiments, an extension limiting band 800 may be stitched to the first and second belt pulley bases 130, 140 at stitching 805. The extension limiting band 800 operates as a limiter for lateral movement of the belt pulley bases 130/140. Also, given that the belt pulley bases are not fastened to a sleeve 105, where the belt arms 122/124 are not placed tightly around the abdomen region of the patient, the belt pulley bases 130/140 undergo slight adjustment when the tightening straps are pulled until slack caused by the improper placement of the belt arms is eliminated, and thereafter, movement of the tightening strap fasteners 190/195 begins to stretch (elongate) the elastic strapping 170.

As this invention is susceptible to embodiments of many different forms, it is intended that the present disclosure is to be considered as an example of the principles of the invention and not intended to limit the invention to the specific embodiments shown and described. Instead, aspects from one embodiment are contemplated to be incorporated in other embodiments.

I. Terminology

In the following description, certain terminology is used to describe aspects of the invention. For example, the term "member" may be construed as a structural component of an orthopedic brace. In certain situations, a member may include a component covered by soft goods such as one or more textiles, one or more fabrics (woven fabrics and/or non-woven fabrics), leathers, and/or another covering material. These soft goods may feature unbroken loop (UBL) fasteners (i.e., "loop" type fasteners) to which a "hook" type fastener may be attached or may feature a hook-type fastener for attachment to a loop-type fastener. In lieu of UBL and hook-type fasteners, it is contemplated that other fastener types may be deployed (e.g., snaps, rivets, adhesive, stitching, etc.).

The term "pocket" is a partial enclosure, namely a structure having partially enclosed perimeter except for an opening.

The term "attach" and other tenses of the term (attached, attaching, etc.) may be construed as physically connecting a first member to a second member. A "fastener" may be construed as any physical component that is used to attach different members together. An illustrative example of different types of fasteners and fastening techniques may include, but are not limited or restricted to snaps, buttons, clasps, buckles, adhesives, sewing, heat sealing (or melting), gluing, knitting, or other physical coupling techniques such as a hook and loop connection.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps, or acts are in some way inherently mutually exclusive.

II. General Architecture

Referring to FIG. 1A, a posterior view of a first embodiment of a brace 100 worn to provide compression against a posterior region of the wearer and provide lifting forces for an abdomen area of the wear for maternity or bariatric application. The brace 100 features a tightening mechanism 110, a pair of belt arms 120 coupled to the tightening mechanism 110, and a padded posterior sleeve 105 slidably placed over the tightening mechanism 110. The padded posterior sleeve 105 may be positioned to partially cover certain components of the tightening mechanism 110, such as belt pulley bases 130/140 and strap pulley bases 150/160 coupled together by elastic strapping 170 as shown in FIG. 1C1-1C2.

Figure 1B:
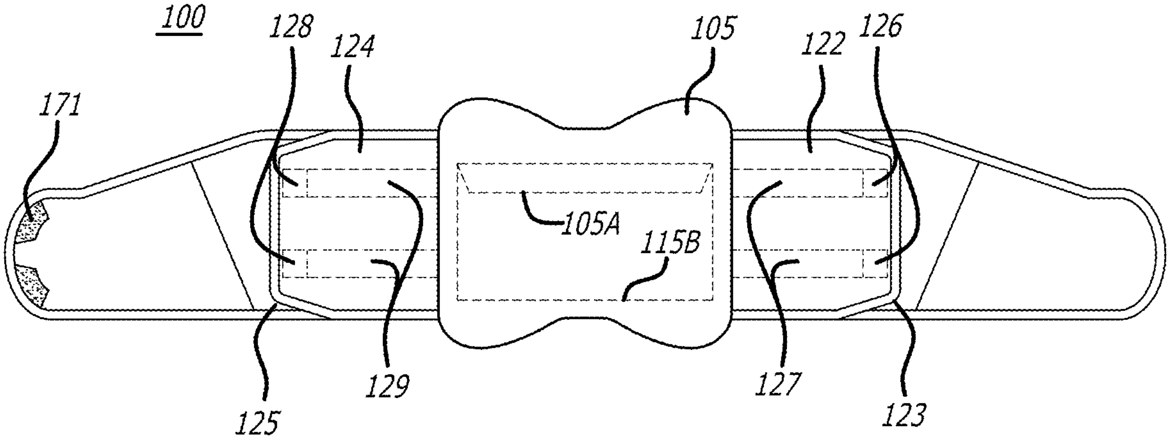
FIG. 1B is an anterior view of the brace 100 according to an implementation of the disclosure.

As shown in FIGS. 1A-1B, a first belt arm 122 of the pair of belt arms 120 is coupled to a first belt pulley base 130 of the tightening mechanism 110 by (i) inserting a first end 123 of the first belt arm 122 through a first elongated slot 131 of the first belt pulley base 130 and (ii) folding the inserted portion over a remainder of the first belt arm 122. As shown in FIG. 1C1-1C2, a second belt arm 124 may be coupled to a second belt pulley base 140 by insertion of an end 125 of the second belt arm 124 through a first elongated slot 141 of the second belt pulley base 140. Although not shown in detail, the first belt pulley base 130 may be configured with a first set of pulleys 132 (e.g., two or more pulleys), which are adapted to receive a first cord segment 175. As an optional feature, as described below in FIG. 8A, the first belt pulley base 130 may be configured with a second slot adapted as a termination point for an extension limiting band to establish a maximum lateral separation 815 between the first and second belt pulley bases 130 and 140.

A first tightening strap 180 features a first end 181 and a second end 182. The first end 181 is securely coupled to an end region of the first belt arm 122, which forms an interior surface of a pocket 183 having a slot 183A through which the first tightening strap 180 extends. The connection of the first end 181 of the first tightening strap 180 is discussed in detail below at least with respect to FIGS. 10A-11K. An outer surface 184 of the pocket 183 includes unbroken loop (UBL) fastener. The second end 182 of the first tightening strap 180 is inserted through a first tightening strap fastener 190 and folded over itself for attachment thereto. As a result, when forces in a first lateral direction (D1) are applied to the first tightening strap 180, the first tightening strap fastener 190 is pulled in the first lateral direction, causing the first cord segment 175 to be extended distally, which shortens a distance between the first belt pulley base 130 and the first strap pulley base 150. As the first strap pulley base 150 moves in the first lateral direction, the elastic strapping 170, positioned between the first and second strap pulley bases 150 and 160, becomes elongated and applies compression to a lower back of the wearer.

Similarly, a second tightening strap 185 is constructed in the same manner as the first tightening strap 180. The second tightening strap 185 features first end 186 and a second end 187. The first end 186 is securely coupled to an end region of the second belt arm 124, which forms an interior surface of a pocket 188 having a slot 188A through which the second tightening strap 185 extends. The connection of the first end 186 of the second tightening strap 185 is discussed in detail below at least with respect to FIGS. 10A-11K. An outer surface 189 of the pocket 188 includes unbroken loop (UBL) fastener. The second end 187 of the second tightening strap 185 is inserted through a second tightening strap fastener 195 and folded over itself for attachment thereto. As a result, when forces in a second lateral direction (D2) are applied to the second tightening strap 185, the second tightening strap fastener 195 is pulled in the second lateral direction, causing a second cord segment 177 to be extended distally, which shortens a distance between the second belt pulley base 140 and the second strap pulley base 160. As the second strap pulley base 160 moves in the second lateral direction, the elastic strapping 170 becomes elongated and applies compression to a lower back of the wearer.

Referring now to FIG. 1B, an anterior view of the brace 100 is shown. After insertion through the first elongated slot 131, the first end 123 is folded over a remainder of the first belt arm 122 so that a first fastening element 126 (e.g., hook fastener) positioned on a first region on an inner surface of the first belt arm 122 is removably attached to a second fastening element 127 complementary to the first fastening element 126. The second fastening element 127 is positioned within a second region on the inner surface of the first belt arm 122, which is different from the first region of the inner surface.

Likewise, after insertion through the first elongated slot 141 of the second belt pulley base 140, the end 125 is folded over a remainder of the second belt arm 124 so that a third fastening element 128 (e.g., hook fastener) positioned on a first region on an inner surface of the second belt arm 124 is removably attached to a fourth fastening element 129 complementary to the third fastening element 128. The fourth fastening element 129 is positioned within a second region on the inner surface of the second belt arm 124, which is different from the first region of the inner surface.

Referring to FIG. 1C1, a first illustrative embodiment of the tightening mechanism 110 of FIGS. 1A-1B, which is coupled to the pair of belt arms 120, is shown. Herein, the tightening mechanism 110 includes the first belt pulley base 130, the second belt pulley base 140, the first strap pulley base 150, the second strap pulley base 160, the elastic strapping 170, the first cord segment 175 with a first tightening strap fastener 190 and a second cord segment 177 with a second tightening strap fastener 195. As shown, the first belt pulley base 130 features the first elongated slot 131 adapted to receive the first end 123 of a first belt arm 122, which is inserted therethrough and folded over for reattachment to the first belt arm 122.

The first strap pulley base 150 features a first slot 152, first and second anchors 153 and 154, and a second set of pulleys 155. The first slot 152 is adapted to receive a first strap 172 with ends coupled to an inner or outer surface of the second strap pulley base 160. At a medial side of the first slot 152, the first strap 172 may receive stitching for better retention of the first strap 172 with the first slot 152.

The first cord segment 175 includes a first end 176*a* attached to a first anchor 153 and a second end 176*b* attached to the second anchor 154. The first cord segment 175 is threaded from the first end 176*a* secured to the first anchor 153 to a first pulley 135 of the first set of pulleys 132, where the first cord segment 175 extends from the first pulley 135 to a first pulley 156 of the second set of pulleys 155. Thereafter, the first cord segment 175 is threaded through an end of the tightening strap fastener 190 and threaded to a second pulley 157 of the second set of pulleys 155 positioned on the first strap pulley base 150. As a result, the first tightening strap fastener 190, in a resting state, resides between the first and second pulleys 156 and 157. The first cord segment 175 continues from the second pulley 157 to a second pulley 137 of the first set of pulleys 132 before returning for attachment to the second anchor 154 located within the first strap pulley base 150.

Referring now to FIG. 1C2, the second cord segment 177 includes a first end 178*a* attached to a first anchor 163 and a second end 178*b* attached to the second anchor 164. The second cord segment 177 is threaded from the first end 178*a* secured to the first anchor 163 to a first pulley 145 of the second set of pulleys 142, where the first cord segment 177 extends from the first pulley 145 to a first pulley 166 of the second set of pulleys 165. Thereafter, the first cord segment 177 is threaded through an end of the second tightening strap fastener 195 and threaded to a second pulley 167 of the second set of pulleys 165 positioned on the second strap pulley base 160. As a result, the second tightening strap fastener 195, in a resting state, resides between the first and second pulleys 166 and 167. The second cord segment 177 continues from the second pulley 167 to a second pulley 147 of the second set of pulleys 142 before returning for attachment to the second anchor 164 located within the second strap pulley base 160.

The second strap pulley base 160 features a second slot 162, first and second anchors 163 and 164, and a second set of pulleys 165. The second slot 162 is adapted to receive a second strap 171 with ends coupled to an inner or outer surface of the second strap pulley base 150. At a medial side of the second slot 162, the second strap 171 may receive stitching for better retention of the second strap 171 with the second slot 162. Stitching of the first and second straps 171, 172 is shown as stitching 205 in at least FIGS. 2A-2B. While the stitching provides the technical advantage of providing equal stretching/balance of straps 171/172 on the superior and inferior regions of the straps 171, 172, it should be understood that stitching at the medial sides thereof is optional and not required in all embodiments.

FIG. 1C1-1C2 illustrate the elastic strapping 170 in a crossing scheme where the first strap 171 is positioned under the second strap 172. In other embodiments, the orientation may be reversed. Further, FIG. 1C1-1C2 illustrate that. The straps 171, 172 are stitched to the underside of the strap pulley bases 150, 160. However, in other embodiments, the straps 171, 172 may be stitched to the upper side of the strap pulley bases 150, 160. For instance, stitching the straps 171, 172 to the upper side of the strap pulley bases 150, 160 may serve to create a slight downward force on the strap pulley bases 150, 160 as the tightening straps 180, 185 are pulled outward and the elastic strapping 170 is moved into an expanded (stretched) state.

Figure 1D:
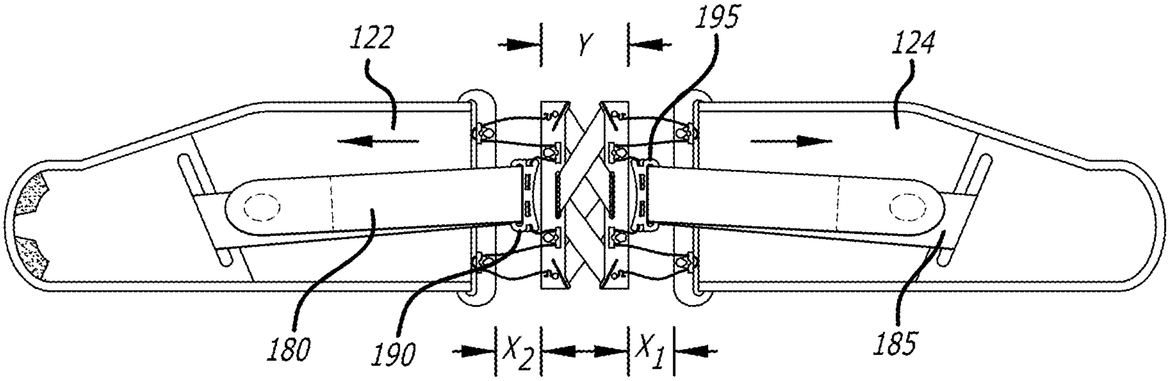
FIG. 1D is a posterior view of the padded posterior sleeve 105 according to an implementation of the disclosure.
Figure 1D:
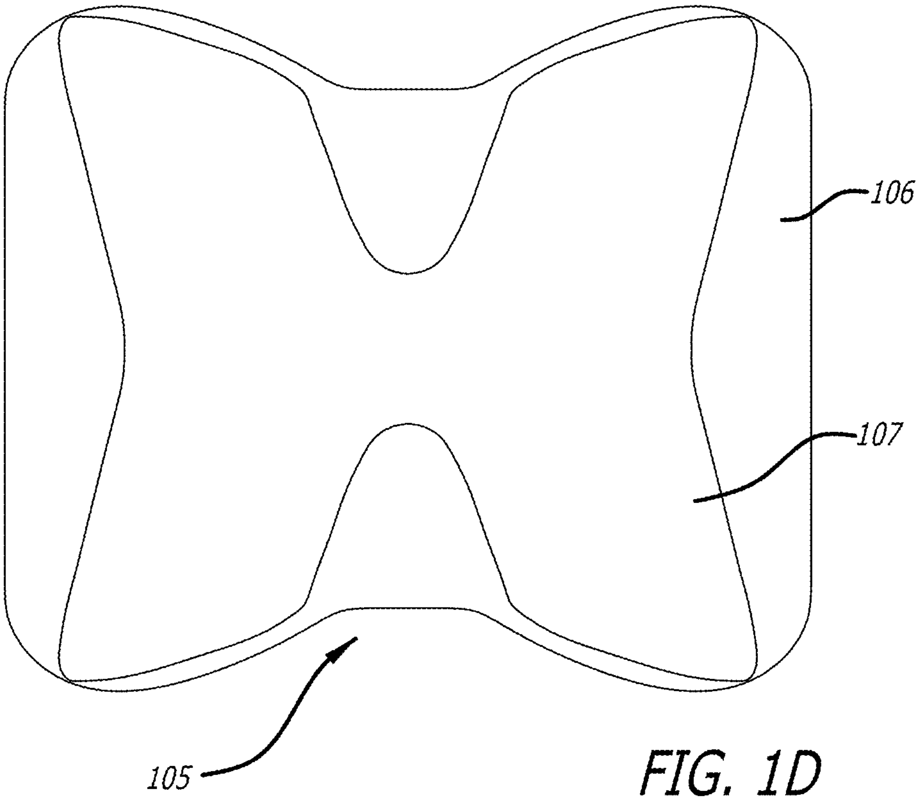

Referring now to FIG. 1D, a posterior view of the padded posterior sleeve 105 is shown according to an implementation of the disclosure. As shown in FIGS. 1A-1B, the tightening mechanism 110 may be positioned within the padded posterior sleeve 105. The padded posterior sleeve 105 may be compromised of an anterior layer 106, e.g., configured to rest against a wearer's back and a posterior layer 107 configured to be externally (outwardly) facing. The anterior layer 106 and the posterior layer 107 may take different shapes or designs, with some designs providing visibility or partial visibility to the tightening mechanism 110, while others, such as the embodiment shown in FIGS. 1A-1B, and 1D provide little to no visibility. The anterior layer 106 may be filled with a foam padding and/or a rigid or semi-rigid plastic panel to provide cushioning, support, and comfort. Example foam padding materials include polyethylene foam (PE foam), polyurethane foam (PU foam), memory foam (Viscoelastic foam), neoprene foam, etc. In some embodiments, silicone gel may be utilized individually or in combination with a foam padding material.

The padded posterior sleeve 105 provides comfort for the wearer through the presence of the foam padding within the anterior layer 106 between the wearer's back and the tightening mechanism 110. Additionally, the posterior layer 107 serves to protect the tightening mechanism 110 by, for example, preventing the cord segments 175, 177 from getting caught on objects and shielding the belt pulley bases 130, 140 and the strap pulley bases 150, 160 from objects such as chair backs, walls, or other surfaces an individual's back routinely contacts on a daily basis.

Briefly referring back to FIG. 1B, the inner side of the anterior layer 106 (e.g., the inwardly facing side configured to contact a wearer) may include a slit or other opening that provides access to an internal pocket 105B within the anterior layer 106, where the slit that may be closed or covered by a flap 105A. The internal pocket 105B may be configured to receive a hot/cold therapy pack ("a thermal therapy pack"), which in some examples may be a gel pack. The thermal therapy pack that may be configured to provide hot/cold therapy to the wearer. Examples of hot/cold therapy packs include gel packs that may be refrigerated/frozen or heated, instant ice or heat packs (chemical packs) that are single use and generate heat or cold in response to a chemical reaction inside the pack (such as be squeezing or shaking the pack), clay or bead packs that may be refrigerated/frozen or heated, etc. The hot/cold therapy packs provide heat and/or cold therapy, helping to reduce pain, inflammation, and muscle stiffness.

Figure 3:
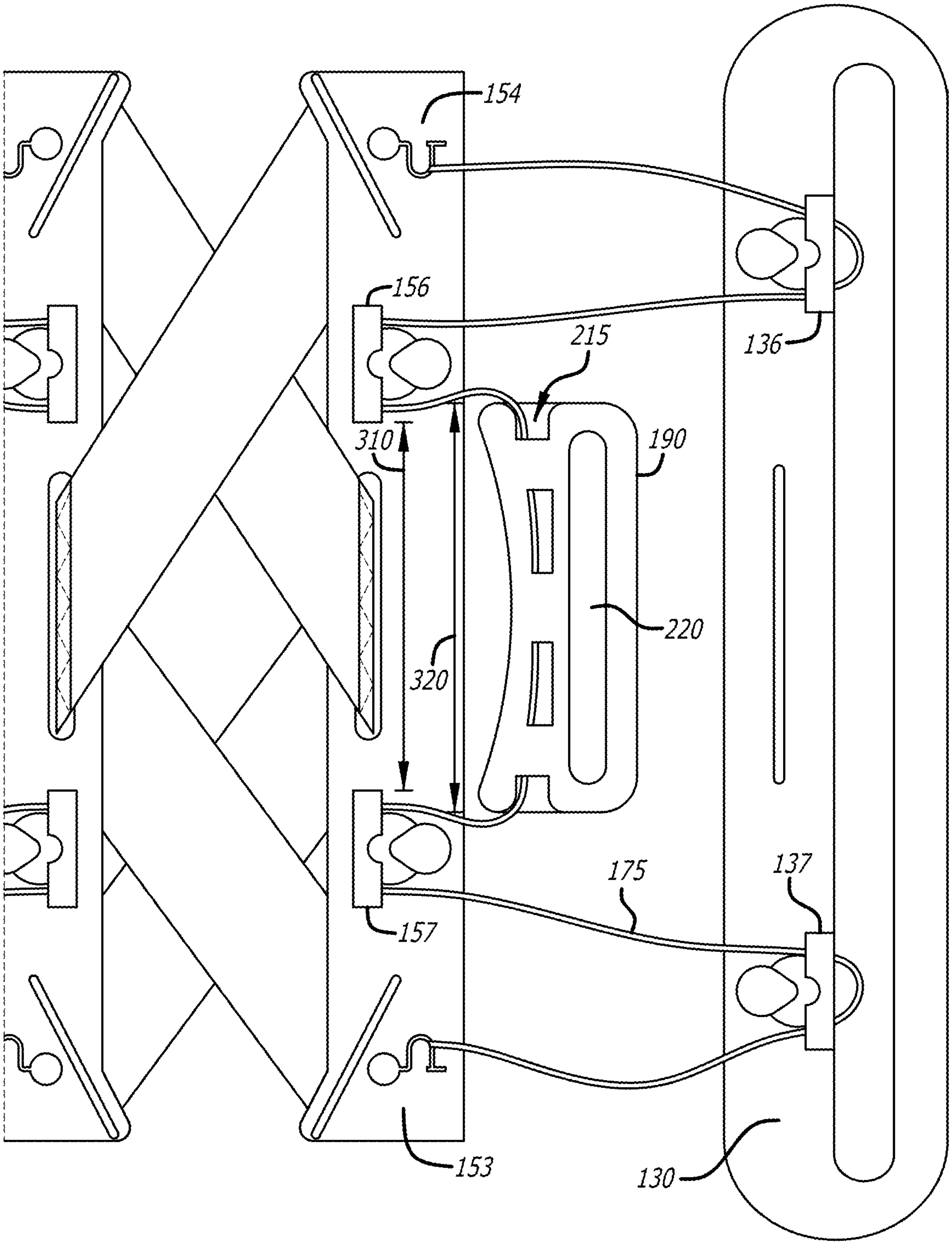

FIG. 1C3 provides an illustration of the directions each of the belt pulley bases 130, 140 and the strap pulley bases 150, 160 move in response to the tightening of the brace 100 when the tightening straps 180, 185 are pulled outwardly. As shown, the outward pulling of the tightening straps 180, 185 initially pulls the tightening strap fasteners 190, 195 in the outward direction opposite one another, which pulls on the cord segments 175, 177 respectively, which shortens the distances $X_1$-$X_2$. As the distances $X_1$-$X_2$ decrease, continued tightening of the tightening straps 180, 185 engages the elastic strapping 170 by bringing such into an extended (stretched) state, which increases the distance Y.

Figure 2A:
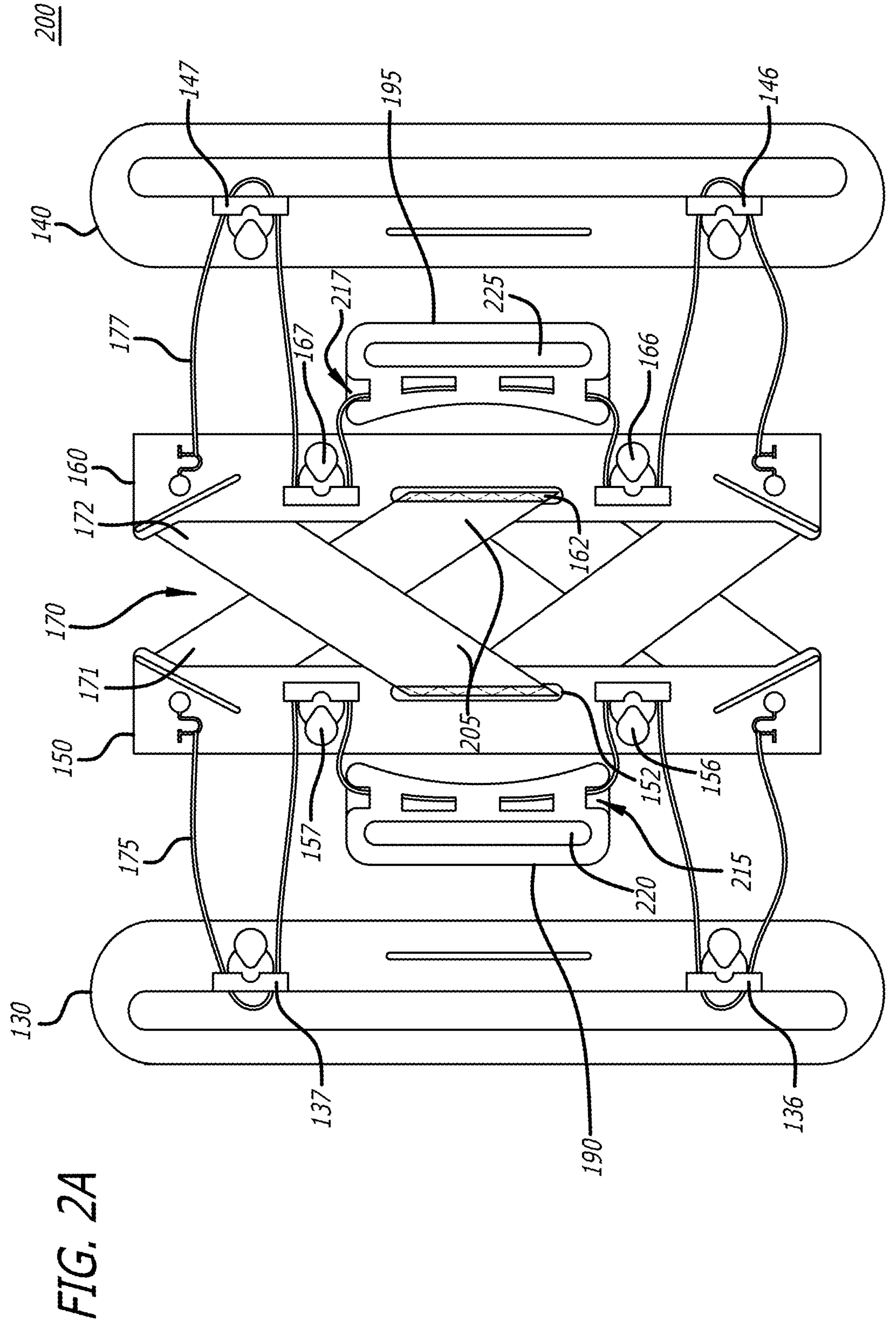
FIG. 2A is a posterior view of the tightening mechanism 110 according to an implementation of the disclosure.

Referring now to FIG. 2A, a posterior view of the tightening mechanism 110 is shown according to an implementation of the disclosure. The detailed view 200 of FIG. 2A illustrates the components of the tightening mechanism 110 without coupling to belt arms 122, 124 or tightening straps 180, 185. As discussed above, the tightening mechanism 110 is comprised of first and second belt pulley bases 130, 140 and first and second strap pulley bases 150, 160. The first belt pulley base 130 is coupled to the first strap pulley base 150 via a first cord segment 175 that is anchored to the first strap pulley base 150 and threadably interlaced through a series of pulleys disposed on either the first belt pulley base 130 or the first strap pulley base 150 and the first tightening strap fastener 190 as discussed above before terminating at an anchoring point on the first strap pulley base 150.

The detailed view 200 of FIG. 2A further illustrates that the second belt pulley base 140 is coupled to the second strap pulley base 160 via a second cord segment 177 that is anchored to the second strap pulley base 160 and threadably interlaced through a series of pulleys disposed on the second belt pulley base 140 or the second strap pulley base 160 and the second tightening strap fastener 195 as discussed above before terminating at an anchoring point on the second strap pulley base 160. Further, the first and second strap pulley bases 150, 160 are coupled via an elastic strapping 170 that is comprised of straps 171, 172. In some embodiments, as shown in FIG. 2A, the straps 171, 172 may each be stitched to the first and second strap pulley bases 150, 160, respectively, at first and second ends and a medial section (e.g., medial stitching 205).

FIG. 2A also provides illustrative detail as to each of the first and second tightening strap fasteners 190, 195. In particular, the first tightening strap fastener 190 includes a lumen 215 through which a portion of the first cord segment 175 passes and a slot 220 through which the first tightening strap 180 passes. Similarly, the second tightening strap fastener 195 includes a lumen 217 through which a portion of the second cord segment 177 passes and a slot 225 through which the second tightening strap 185 passes.

Figure 2B:
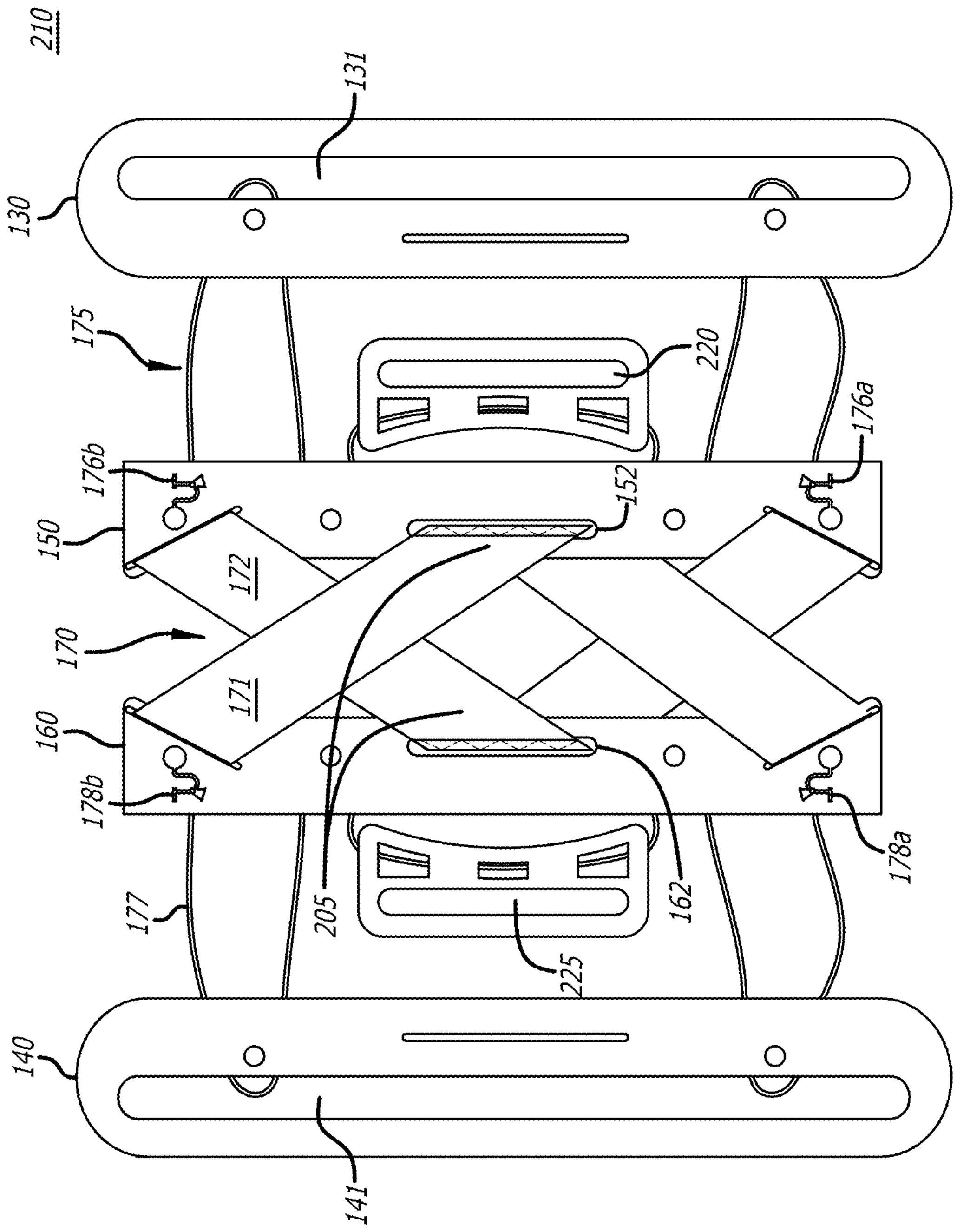
FIG. 2B is an anterior view of the tightening mechanism 110 according to an implementation of the disclosure.

Referring to FIG. 2B, an anterior view of the tightening mechanism 110 is shown according to an implementation of the disclosure. The detailed view 210 of FIG. 2B illustrates the same components as included in FIG. 2A. While FIG. 2B illustrates that the straps 171, 172 may be stitched to an inner side of the first and second strap pulley bases 150, 160, respectively, the straps 171, 172 may be stitched to the outer side of the first and second strap pulley bases 150, 160, respectively, as noted above.

Referring to FIG. 3, a detailed posterior view of a portion of the tightening mechanism 110 illustrating an alignment of the first tightening strap fastener 190 and first and second pulleys 156 and 157 is shown according to an implementation of the disclosure. The detailed view of FIG. 3 illustrates that the first tightening strap fastener 190 may be sized according to the spacing of the first and second pulleys 156 and 157. As shown, the first tightening strap fastener 190 has a width 320 that is substantially equivalent to the distance 310 separating the first and second pulleys 156 and 157. As a result, when the first cord segment 175 is in a relaxed state (e.g., not taut), the first tightening strap fastener 190 may be positioned in substantial alignment with the inner edges of the first and second pulleys 156 and 157. As the first tightening strap fastener 190 is pulled outward away from the first and second pulleys 156 and 157, the first cord segment 175 is lead outwardly due to being threaded through the lumen 215.

Figure 4:
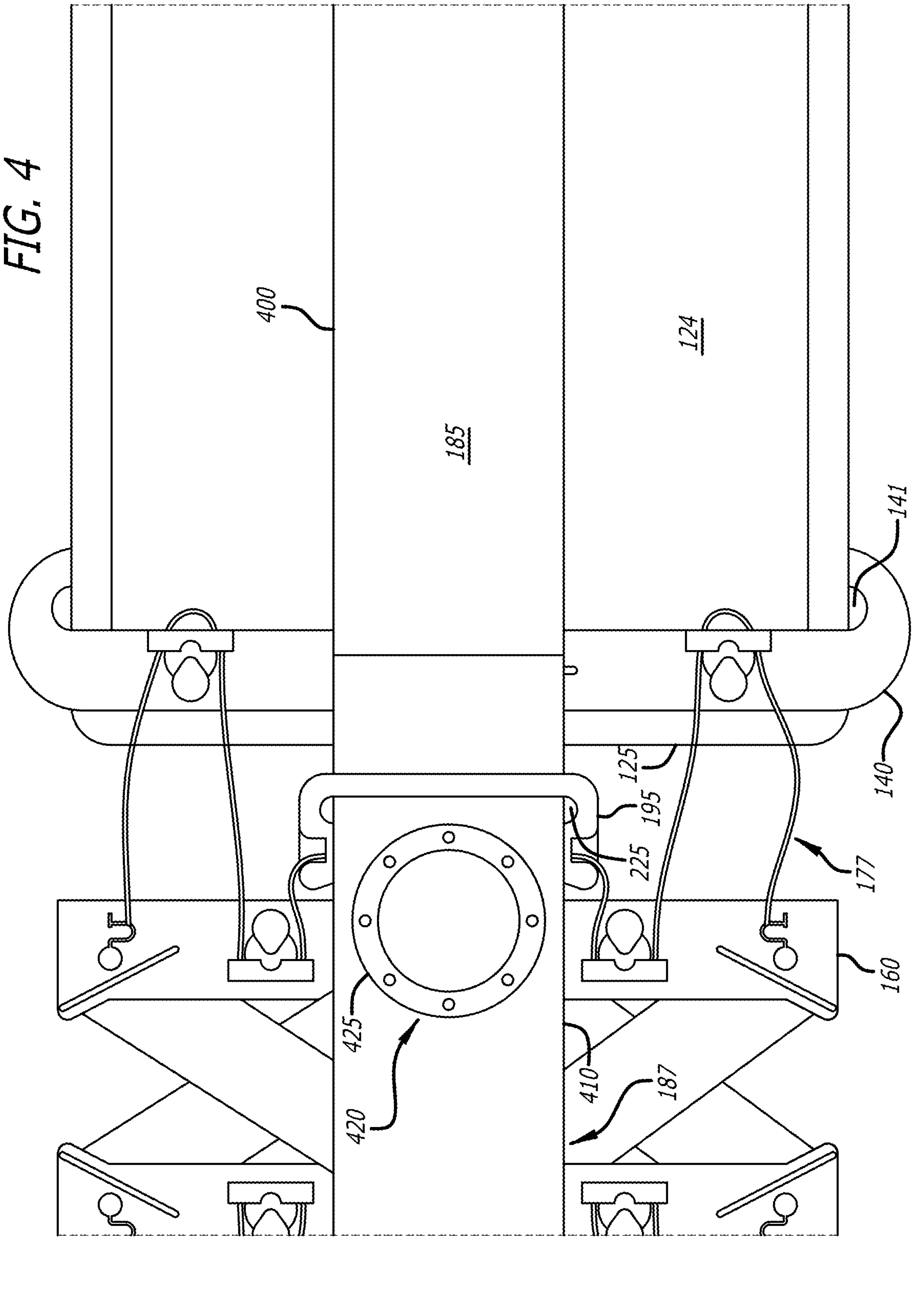
FIG. 4 is a detailed posterior view of a portion of the tightening mechanism 110 including portions of the second tightening strap 185 and the second belt arm 124 threaded through the second tightening strap fastener 195 and a second belt pulley base 140, respectively according to an implementation of the disclosure.

Referring to FIG. 4, a detailed posterior view of a portion of the tightening mechanism 110 including portions of the second tightening strap 185 and the second belt arm 124 threaded through the second tightening strap fastener 195 and a second belt pulley base 140, respectively is shown according to an implementation of the disclosure. The end 125 of second belt arm 124 is shown partially inserted through the first elongated slot 141 of the second belt pulley base 140. As seen in FIG. 1B, the end 125 of the second belt arm 124 is folded over onto the inner side of the second belt arm 124 such that third fastening element 128 is coupled with fourth fastening element 129 to securely coupled the second belt arm 124 to the second belt pulley base 140.

Additionally, FIG. 4 illustrates the second end 187 of second tightening strap 185 partially inserted through the slot 225 of the second strap fastener 195. The second end 187 may include an opening 420 into which a wearer may insert their thumb to pull the second tightening strap 185 easily outwardly (away from the second tightening strap fastener 195). The opening 420 may include a reinforcement component 425 coupled around its edging, where the reinforcement component 425 may be comprised of silicone or rubber or rigid or semi-rigid plastic that prevents fraying or ripping of the edging of the opening 420 and also provides comfort to the wearer through a smooth edge. The underside of the second end 187 (shown in FIG. 4) may be comprised of hook fasteners 410 configured to couple with unbroken loop (UBL) 400 of the second tightening strap 185 when the second tightening strap 185 has been pulled to the desired tightness.

Figure 5:
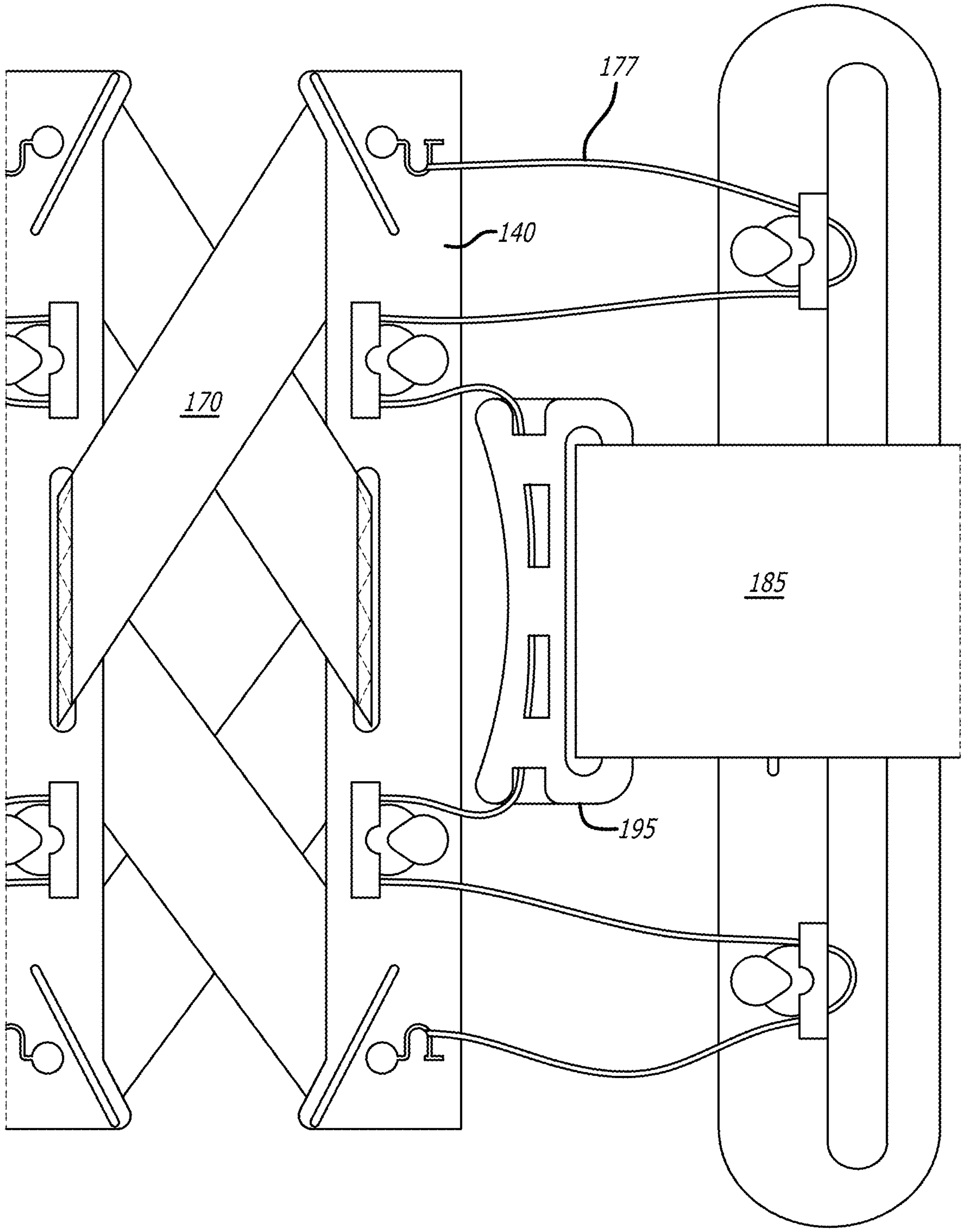
FIG. 5 is a second detailed posterior view of the portion of the tightening mechanism 110 shown in FIG. 4 according to an implementation of the disclosure.

Referring to FIG. 5, a second detailed posterior view of the portion of the tightening mechanism 110 shown in FIG. 4 is provided according to an implementation of the disclosure. FIG. 5 illustrates the second tightening strap 185 folded over to enable coupling of the end of the second tightening strap 185 having hook fasteners to the body of the second tightening strap 185 comprised of UBL.

Figure 6:
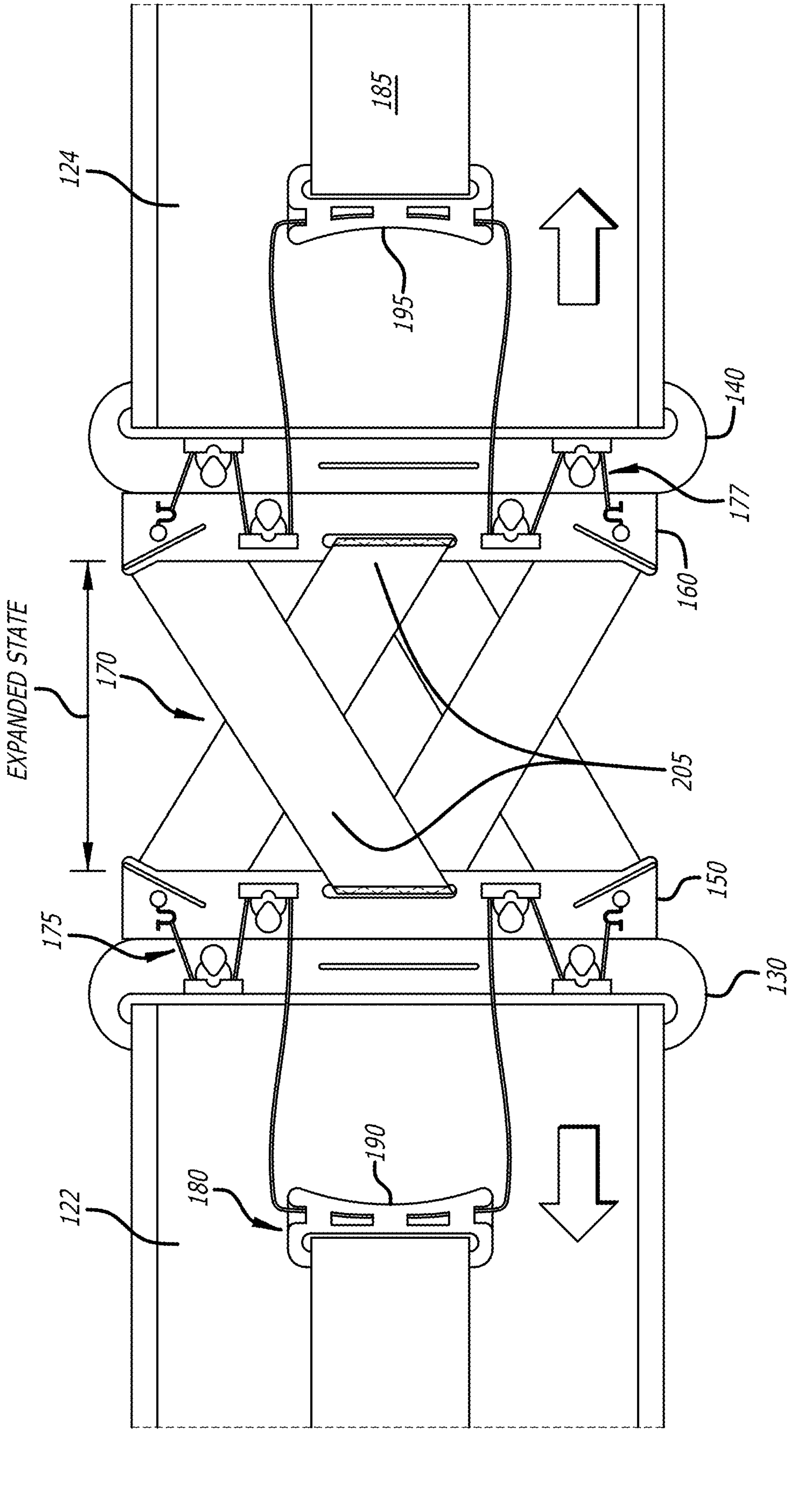
FIG. 6 is a posterior view of a portion of the tightening mechanism 110 in a stretched (expanded) state according to an implementation of the disclosure.

Referring to FIG. 6, a posterior view of a portion of the tightening mechanism 110 in a stretched (extended) state is shown according to an implementation of the disclosure. The detailed view of FIG. 6 illustrates the tightening mechanism 110 in a stretched state as the first and second tightening straps 180, 185 are engaged by a wearer and pulled outwardly, e.g., away from the elastic strapping 170. As discussed throughout the disclosure, following donning of the brace 100 around an individual's torso, as the first and second tightening straps 180, 185 are pulled outwardly, the first and second tightening strap fasteners 190, 195 pull the first and second cord segments 175, 177 outwardly, which causes convergence of (i) the first belt pulley base 130 and the first strap pulley base 150, and (ii) the second belt pulley base 140 and the second strap pulley base 160. Following convergence of (i) the first belt pulley base 130 and the first strap pulley base 150, and (ii) the second belt pulley base 140 and the second strap pulley base 160, as the tightening straps 180, 185 are continued to be pulled outwardly, the elastic strapping 170 is engaged and transitioned from a resting (relaxed) state to a stretched (extended) state as the first and second strap pulley bases 150, 160 are pulled in opposing directions.

Figure 7A:
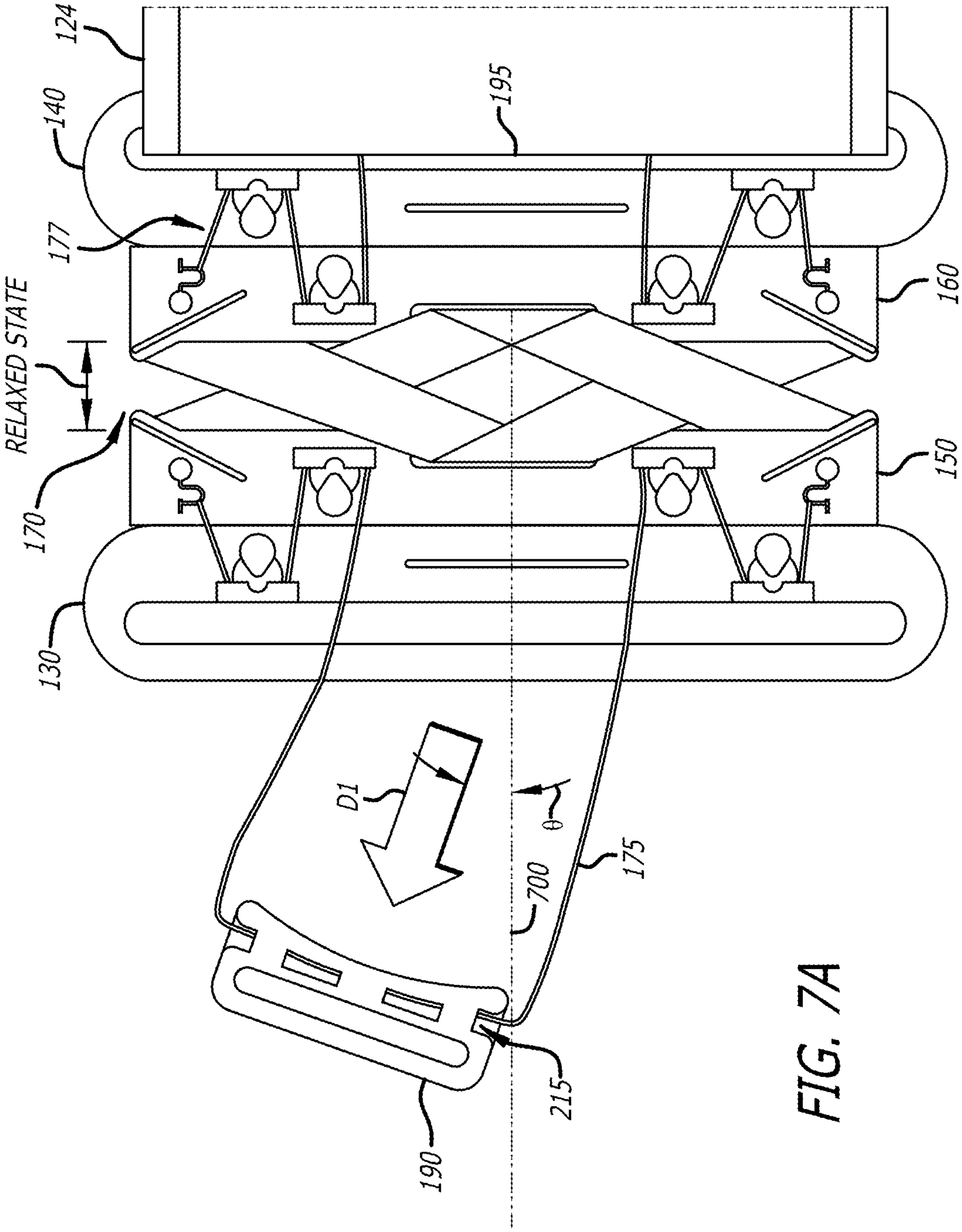
FIG. 7A is a posterior view of the tightening mechanism 110 with the first tightening strap fastener 190 disposed in a first position according to an implementation of the disclosure.

Referring to FIG. 7A, a posterior view of the tightening mechanism 110 with the first tightening strap fastener 190 disposed in a first position is shown according to an implementation of the disclosure. For purposes of clarity, FIG. 7A is illustrated without the first belt arm 122 coupled to the tightening mechanism 110. A central longitudinal axis 700 is illustrated in FIG. 7A and provides a reference point for various directions in which the first tightening strap 180 (not shown in FIG. 7A; see FIG. 1C1-1C3) may be pulled and how such affects the positioning of the first cord segment 175 due to the configuration of the first tightening strap fastener 190. As shown in FIG. 7A, the first tightening strap fastener 190 may be pulled in a first direction D1, which may be at a first angle θ1 relative to the longitudinal axis 700.

Importantly, the configuration of the first tightening strap fastener 190 acts as an additional pulley as the first cord segment 175 is threaded through the lumen 215 and the width 320 of the first tightening strap fastener 190 to substantially match the distance 310 between the pulleys 156, 157 (see FIG. 3). Thus, the first tightening strap fastener 190 directs the first cord segment 175 in the direction D1 and prevents snagging of the first cord segment 175 in the pulleys 156, 157.

Figure 7B:
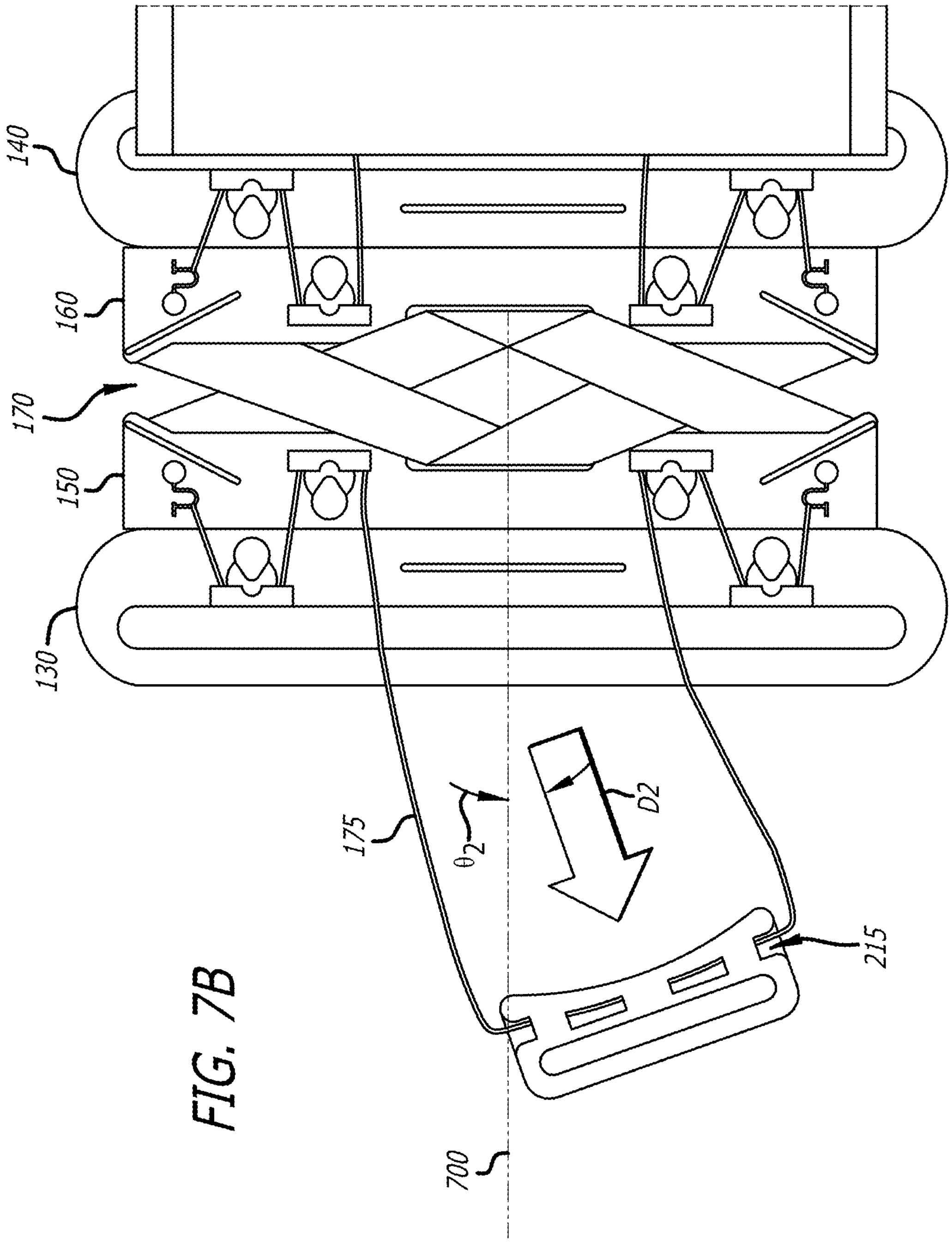
FIG. 7B is a posterior view of the tightening mechanism 110 with the first tightening strap fastener 190 disposed in a second position according to an implementation of the disclosure.

Referring to FIG. 7B, a posterior view of the tightening mechanism 110 with the first tightening strap fastener 190 disposed in a second position is shown according to an implementation of the disclosure. The longitudinal axis 700 is also illustrated in FIG. 7B, which demonstrates that the first tightening strap fastener 190 may be pulled in a second direction D2, which may be at a second angle θ2 relative to the longitudinal axis 700 that is different than the first direction D1 and first angle θ1 of FIG. 7A.

Figure 8A:
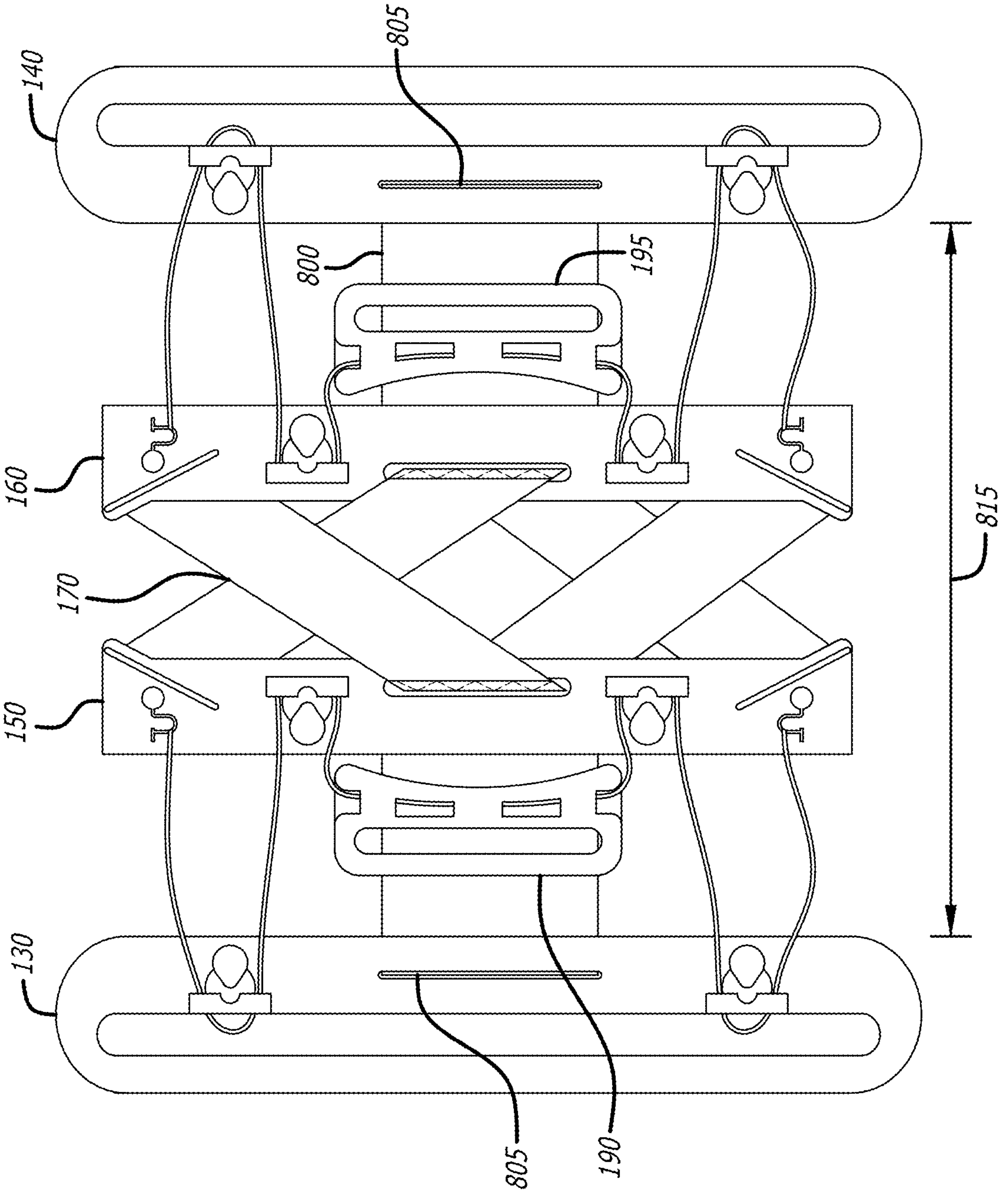
FIG. 8A is a posterior view of a second embodiment of the tightening mechanism 810 including an extension limiting band 800 according to an implementation of the disclosure.
Figure 9A:
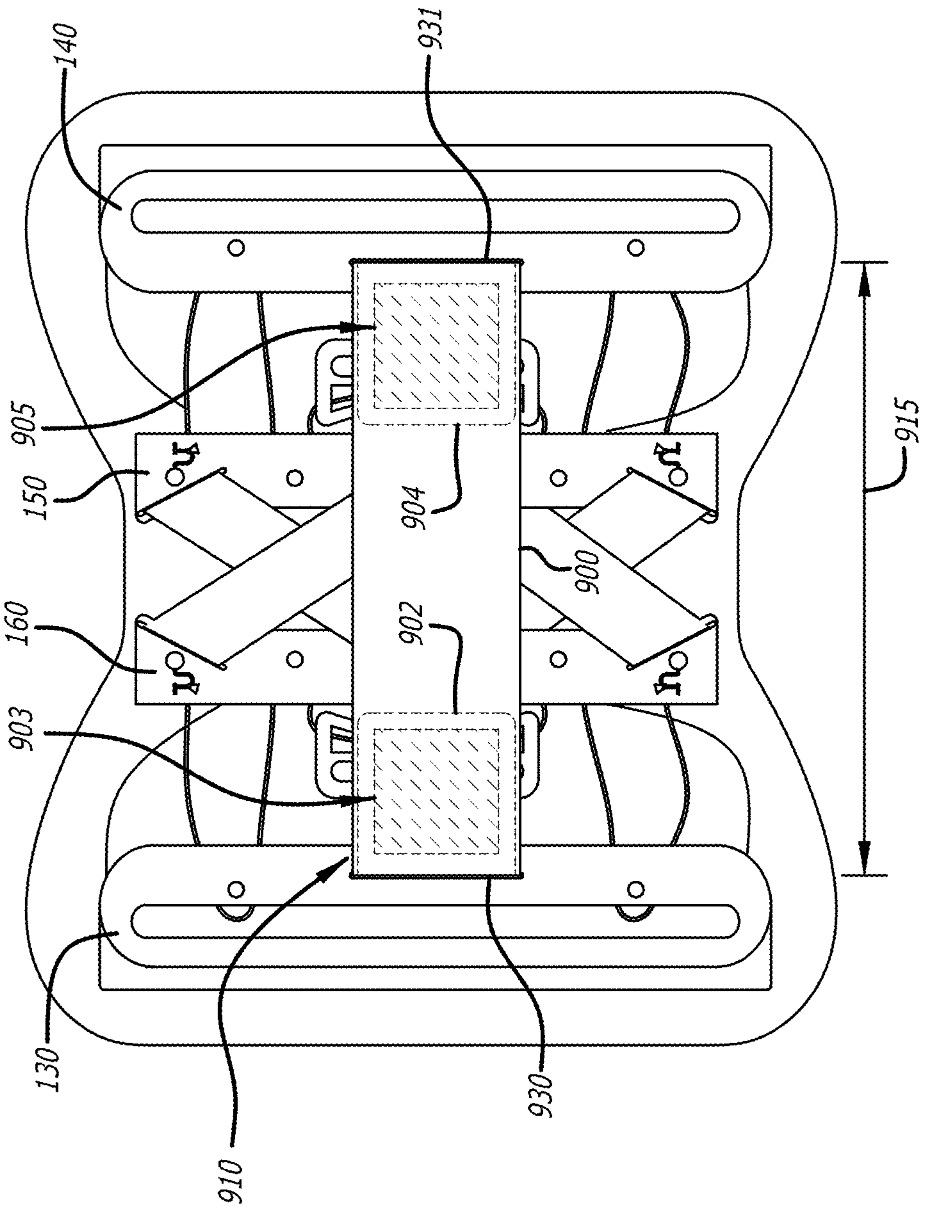
FIG. 9A is a second posterior view of a third embodiment of the tightening mechanism 110 including a view illustrating connection patches of a second embodiment of an extension limiting band 910 that is adjustable in its extension limiting according to an implementation of the disclosure.

Referring to FIG. 8A, a posterior view of a second embodiment of the tightening mechanism 810 including an extension limiting band 800 is shown according to an implementation of the disclosure. The tightening mechanism 810 of FIG. 8A includes many of the same components as the tightening mechanism 110 discussed throughout the disclosure, which have been labeled with like reference numerals. As a result, details of such components may not be repeated. However, aspects of such components will be addressed in relation to the structure and operability of extension limiting band 800. As shown in FIG. 8A, the extension limiting band 800 that is comprised of a non-stretch material, e.g., has minimal to no elasticity, and serves to limit maximum width 815 that the first and second belt pulley bases 130, 140 may separate in opposing directions. FIG. 8A illustrates that the extension limiting band 800 may be stitched to the first and second belt pulley bases 130, 140 at stitching 805. In some embodiments, the extension limiting band 800 may be adhered with an adhesive or permanently coupled via application of heat (e.g., heat sealed) to the first and second belt pulley bases 130, 140. The permanent coupling of the extension limiting band 800 to the first and second belt pulley bases 130, 140 through stitching, adhesive, or the application of heat may collectively be referred to as being "joined" together. However, as shown in FIG. 9A, other embodiments of an extension limiting band may be utilized that do not require stitching 805, e.g., coupling via hook and loop fasteners for example.

The tightening mechanism 810 operates in the same manner as the tightening mechanism 110, e.g., the first and second belt pulley bases 130, 140 couple to first and second belt arms 122, 124 and the first and second strap pulley bases 150, 160 couple to first and second tightening straps 180, 185, and following positioning of the first and second belt arms 122, 124 on a wearer's torso, when the first and second tightening straps 180, 185 are pulled in opposite directions, the cord segments 175, 177 pull the first belt pulley base 130 and the first strap pulley base 150 together and the second belt pulley base 140 and the second strap pulley base 160 together, which stretches the elastic strapping 170 as the first and second strap pulley bases 150, 160 are pulled in opposite directions. During use, the extension limiting band 800 acts to limit how far the first and second strap pulley bases 150, 160 may be pulled in opposite directions, i.e., to the maximum width (or maximum lateral separation) 815. Another use of the extension limiting band 800 is to maintain the tightening mechanism 110 and/or 810 within the posterior sleeve 105 of FIGS. 1A-1B, despite forces being applied to the belt pulley bases 130/140 and the strap pulley bases 150/160. Additionally, the extension limiting band 800 assists to center the tightening mechanism 110 and/or 810 within the posterior sleeve 105.

Figure 8B:
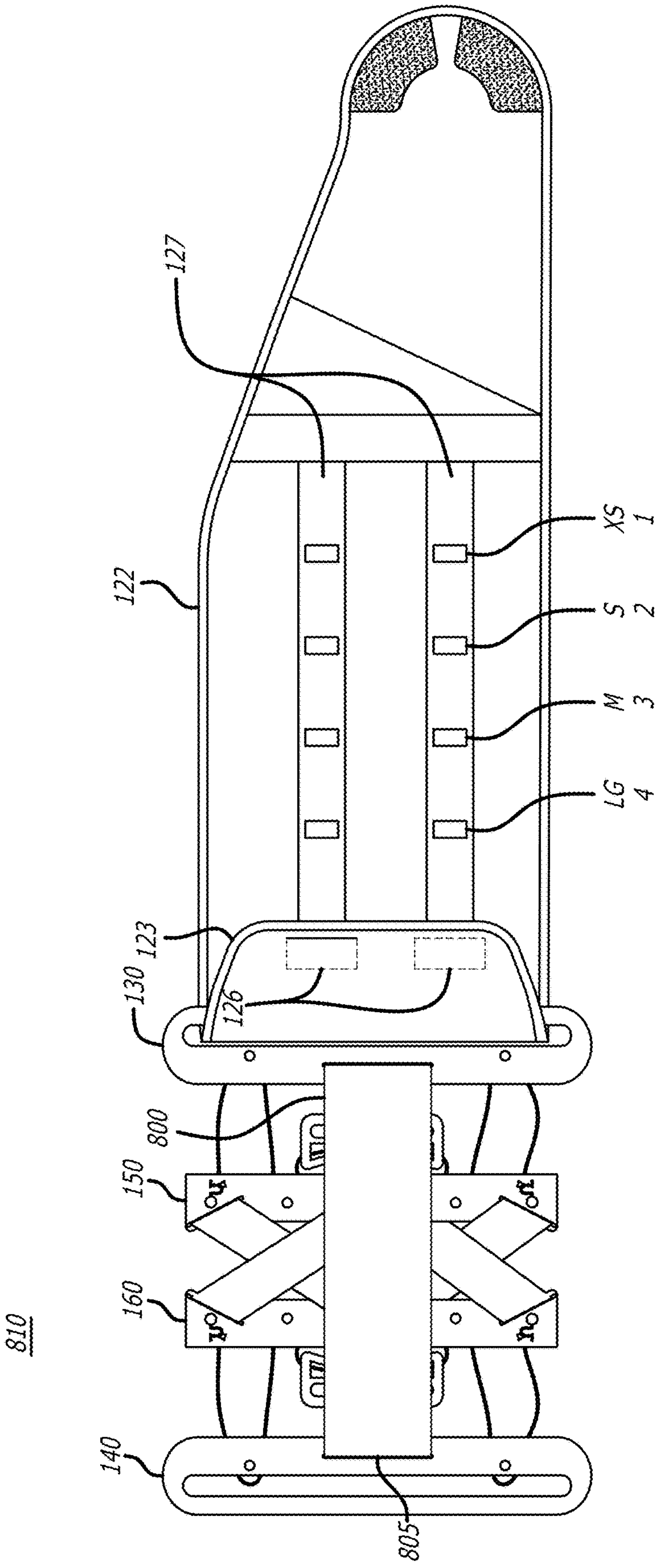
FIG. 8B is an anterior view of the second embodiment of the tightening mechanism 810 including the extension limiting band 800 and illustrating a set of sizing indicators on a first belt arm 122 according to an implementation of the disclosure.

Referring to FIG. 8B, an anterior view of the second embodiment of the tightening mechanism 810 including the extension limiting band 800 and illustrating a set of sizing indicators on a first belt arm 122 is shown according to an implementation of the disclosure. First, FIG. 8B illustrates an inner side of the tightening mechanism 810, which includes the extension limiting band 800 stitched to the first and second belt pulley bases 130, 140 via stitching 805. Also, the extension limiting band 800 may be attached (e.g., stitched or a removable attachment) to the padded posterior sleeve 105.

Second, FIG. 8B illustrates the first belt arm 122 coupled to the first belt pulley base 130. Specifically, the first end 123 of the first belt arm 122 has been threaded through the first elongated slot 131 of the first belt pulley base 130 and folded over onto itself such that first and second fastening elements 126, 127 couple with one another. As discussed in further detail below, the first belt arm 122 includes the first and second fastening elements 126, 127 on the inner side, where the first fastening element 126 is configured to couple with the second fastening element 127, e.g., via hook-and-loop fasteners. The optional sizing indicators illustrated in FIG. 8B serve as a guide to the wearer to size an appropriate size according to the wearer's torso size and also to guide the wearer to set the length of each of the first and second belt arms 122, 124 to a consistent, same size. Example sizing indicators include numbering (e.g., 4, 3, 2, 1, etc.), text (e.g., LG, M, S, XS, etc.), color coding, etc.

Referring to FIG. 9A, a second posterior view of a third embodiment of the tightening mechanism 110 including a view illustrating connection patches of a second embodiment of an extension limiting band 910 that is adjustable in its extension limiting is shown according to an implementation of the disclosure. The tightening mechanism 910 includes many of the same components as the tightening mechanism 110 discussed above and detail as to such component will not be repeated unless as discussed with respect to the structure or functionality of the extension limiting band 900.

The extension limiting band 900 is shown to couple with the first and second pulley bases 130, 140 to limit the maximum width (or maximum lateral separation) 915 between the first and second belt pulley bases 130, 140. While the extension limiting band 800 of FIGS. 8A-8B was shown as being affixed to the first and second belt pulley bases 130, 140 via stitching 805, the extension limiting band 900 is shown as being removably affixed to the first and second belt pulley bases 130, 140. Specifically, the first and second belt pulley bases 130, 140 of FIG. 9A are shown to include elongated slots 930, 931, respectively, through which the extension limiting band 900 extends. The extension limiting band 900 operates such that end portions 902, 904 are configured with connection patches 903, 905 (e.g., subsections of hook fasteners), respectively, that are configured to couple with UBL that forms the majority of the body of the extension limiting band 900. FIG. 9A illustrates that the extension limiting band 900 may be threaded through the elongated slots 930, 931 curling toward the strap pulley bases 150, 160 and coupling to itself.

Figure 9B:
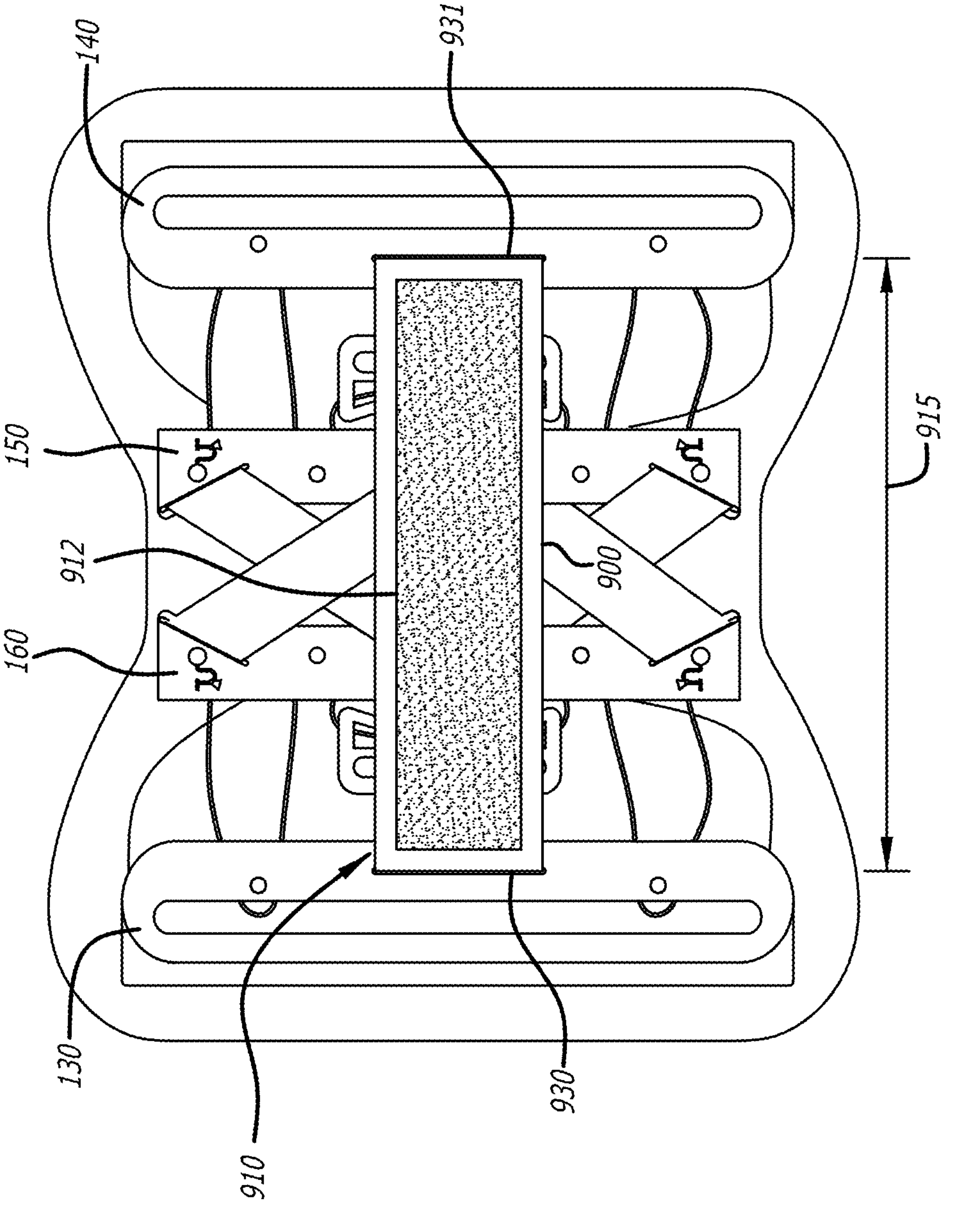
FIG. 9B is a third posterior view of the third embodiment of the tightening mechanism 110 including a view illustrating an exterior-facing connection strip of a second embodiment of an extension limiting band 910 that provides a coupling point with an interior of the sleeve 105 according to an implementation of the disclosure.

FIG. 9B is a third posterior view of the third embodiment of the tightening mechanism 110 including a view illustrating an exterior-facing connection strip of a second embodiment of an extension limiting band 910 that provides a coupling point with an interior of the sleeve 105 is shown according to an implementation of the disclosure. FIG. 9B illustrates the many of same components as shown in FIG. 9A; however, FIG. 9B illustrates the opposite side of the extension limiting band 900, e.g., an exterior-facing side, or stated differently, the side that faces away from the strap pulley bases 150, 160. The exterior-facing side is shown to include a connection strip 912 that may be a subsection of hook fasteners that is configured to couple with an interior side of the sleeve 105, which may be formed of UBL thereby enabling the coupling. The connection strip 912 enables coupling and decoupling of the extension limiting band 900 from sleeve 105, which increases the eases in which the entire tightening mechanism 110 may be coupled to or removed from the sleeve 105. As should be understood, the ability to easily couple the tightening mechanism 110 to the sleeve 105 and decouple the tightening mechanism 110 from the sleeve 105 is a convenient feature for a user when either adjusting the extension limiting band 900 and/or servicing a component of the tightening mechanism 110. However, in other embodiments, the extension limiting band 900 may be sewn to the interior of the sleeve 105, which would permanently couple the extension limiting band 900 to the sleeve 105. Such would be instead of the connection strip 912.

Figure 10A:
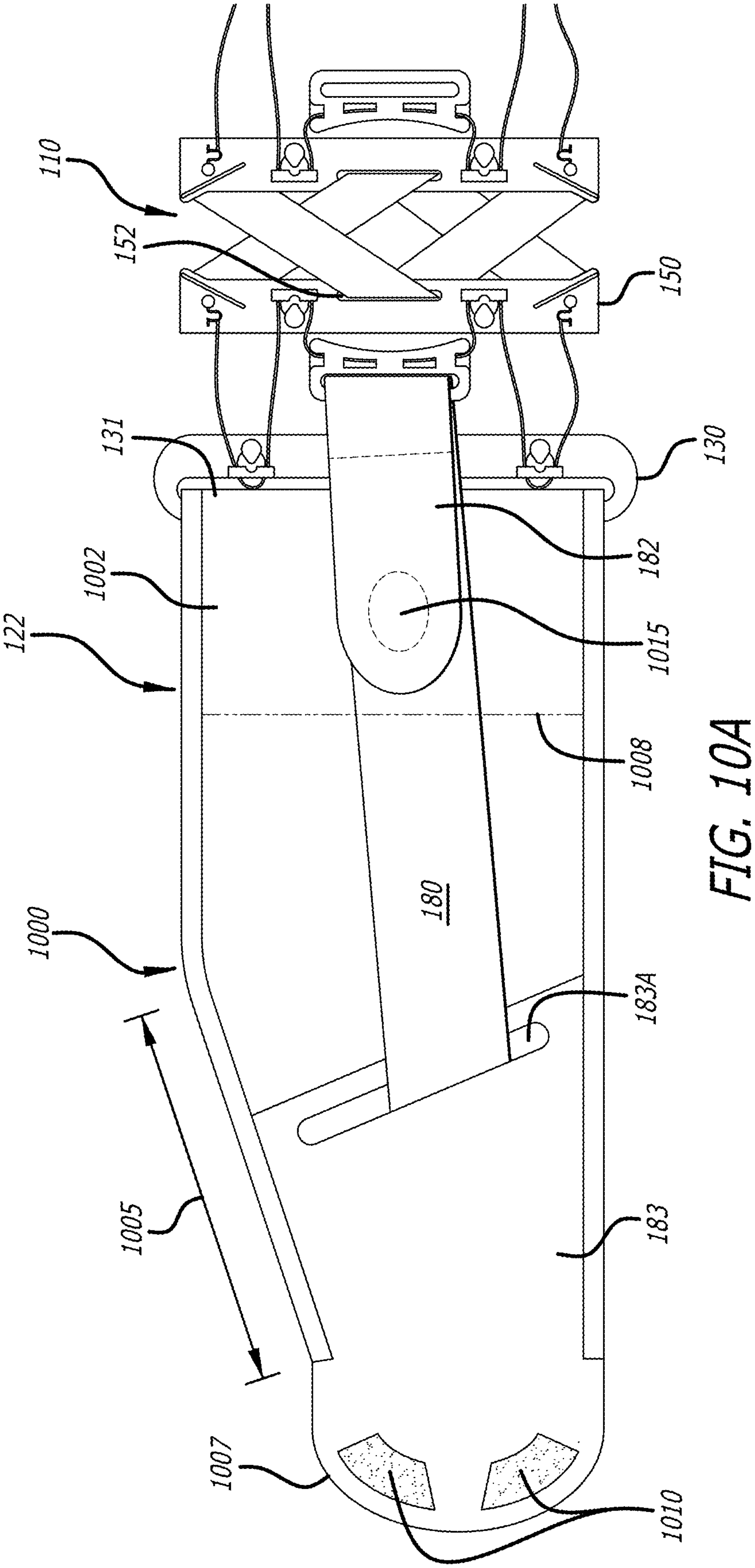
FIG. 10A is a view of an outer side of a first belt arm 122 coupled to the tightening mechanism 110 according to an implementation of the disclosure.

Referring to FIG. 10A, according to an implementation of the disclosure, an exemplary embodiment of an outer side of the first belt arm 122 coupled to the first belt pulley base 130 of the tightening mechanism 110 of FIG. 1C1 is shown. The first belt arm 122 features a reinforced edge 1000 that circumvents a breathable fabric 1002 forming the first belt arm 122. In some embodiments, the reinforced edge 1000 surrounds one or more portions of the circumference of the first belt arm 122 (i.e., less than the entire circumference). In other embodiments, the reinforced edge 1000 surrounds the entire circumference of the first belt arm 122. A segment 1005 of the first belt arm 122 is provided with a downward slope so that a distal end 1007 of the first belt arm 122, which featuring a portion of the pocket 183, has a width that ranges between ¼ and ¾ of the widest width 1008 of the first belt arm 122. The segment 1005 may be referred to as a tapered portion with a tapering toward a distal end of the first belt arm 122. According to this embodiment, the width 1008 of the first belt arm 122 is substantially equivalent to a length of the first elongated slot 131 of the first belt pulley base 130.

Figure 11A:
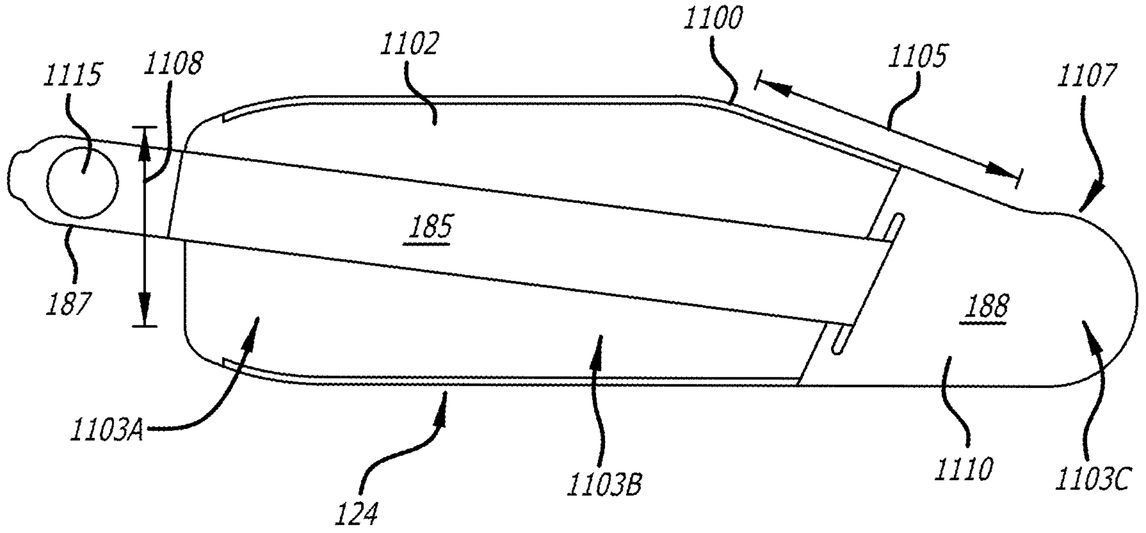
FIG. 11A is a view of an outer side of a second belt arm 124 according to an implementation of the disclosure.
Figure 11B:
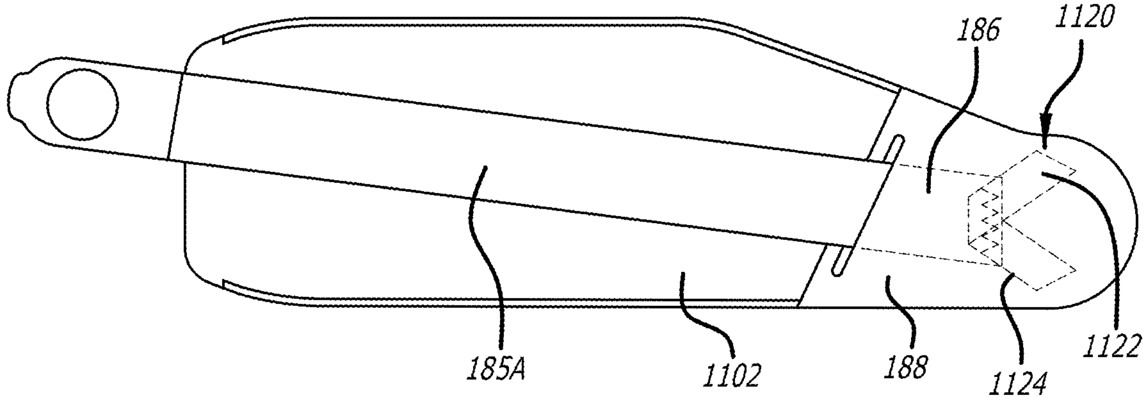
FIG. 11B is a second view of the outer side of the second belt arm 124 illustrating a distal, elastic strap anchoring member 1120 disposed within a distal pocket according to an implementation of the disclosure.
Figure 11C:
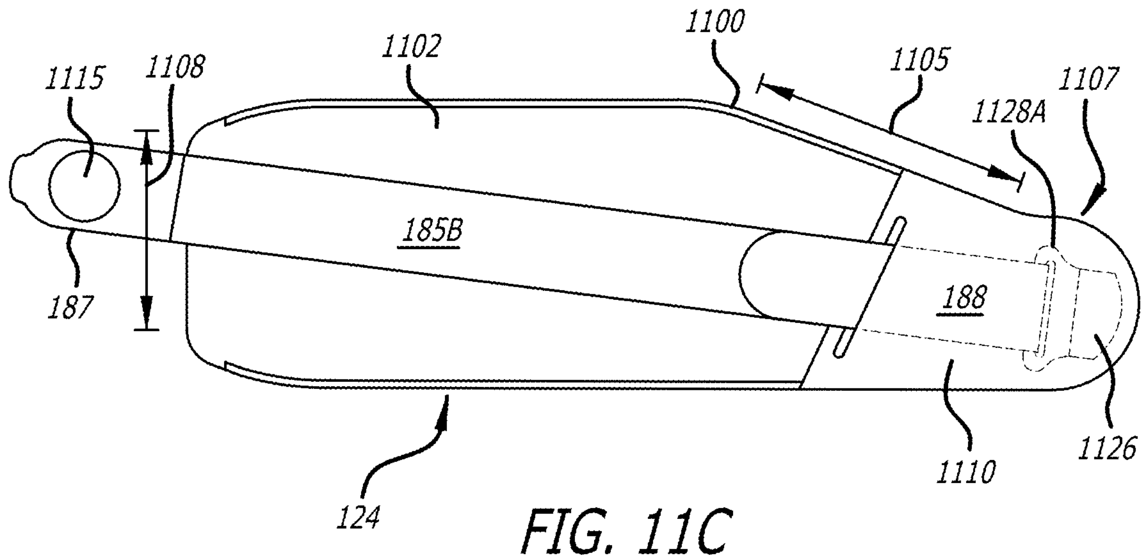
FIG. 11C is a view of a second embodiment of the outer side of the second belt arm 124 according to an implementation of the disclosure.
Figure 11D:
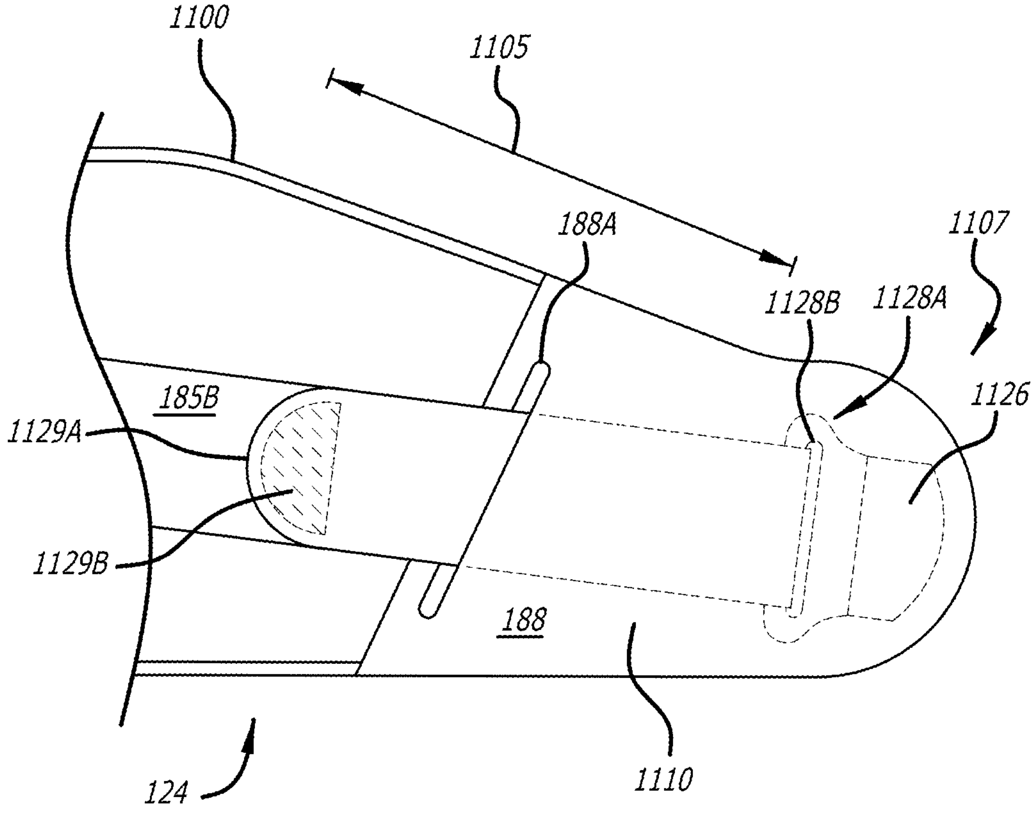
FIG. 11D is a detailed view of the distal end of the second belt arm 124 depicting the second embodiment of FIG. 11C according to an implementation of the disclosure.
Figure 11E:
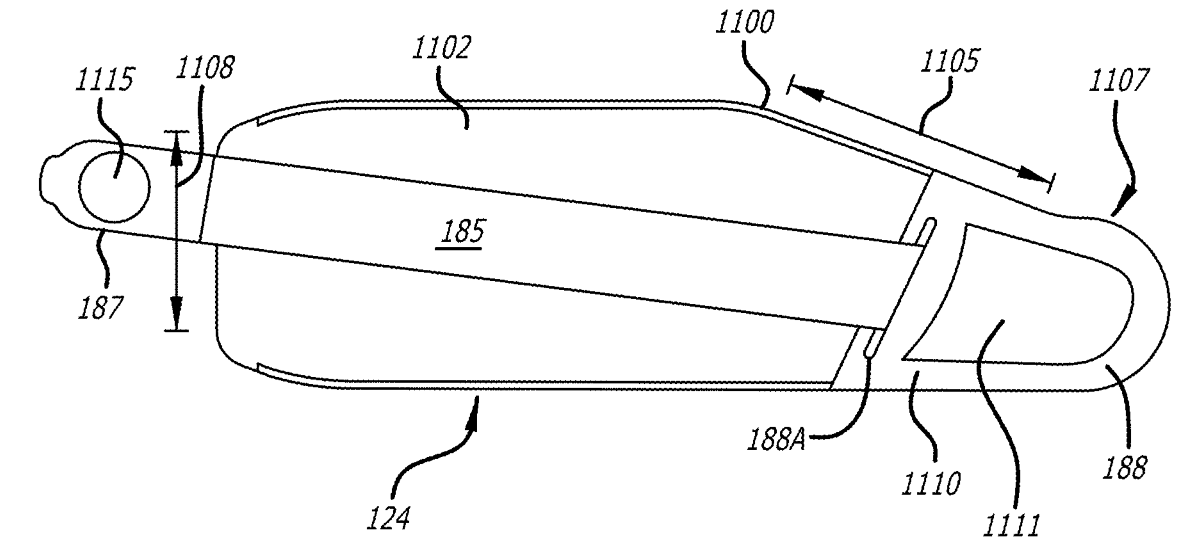
FIG. 11E is a view of a first embodiment of an outer (or posterior) side of a second belt arm 124 having an additional exterior pocket 1111 according to an implementation of the disclosure.
Figure 11F:
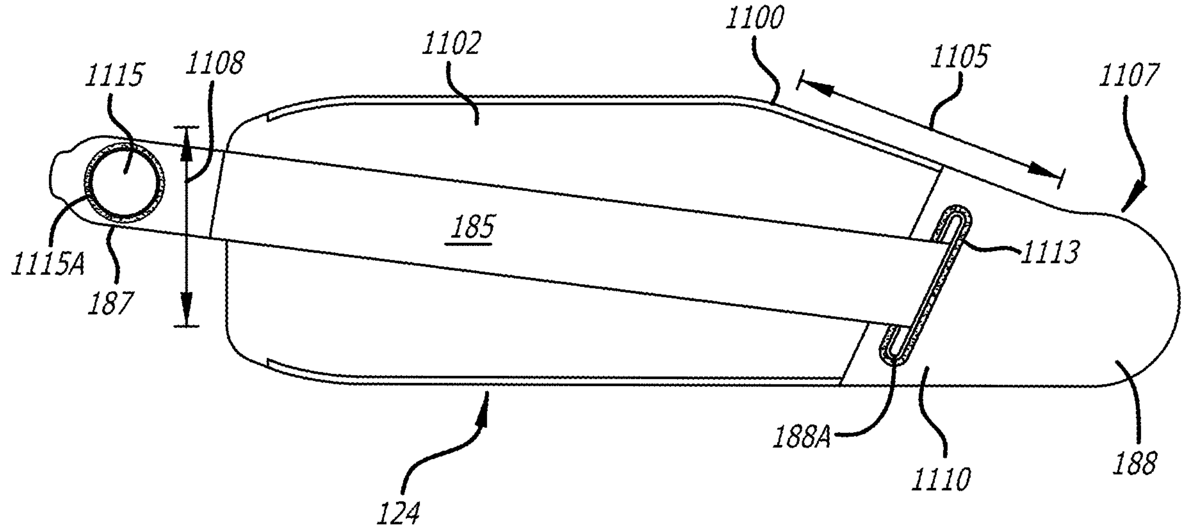
FIG. 11F is a view of a second embodiment of an outer (or posterior) side of a second belt arm 124 having a reinforced edging 1113 around a slot 188A in a pocket 188 of the belt arm 124 according to an implementation of the disclosure.
Figure 11G:
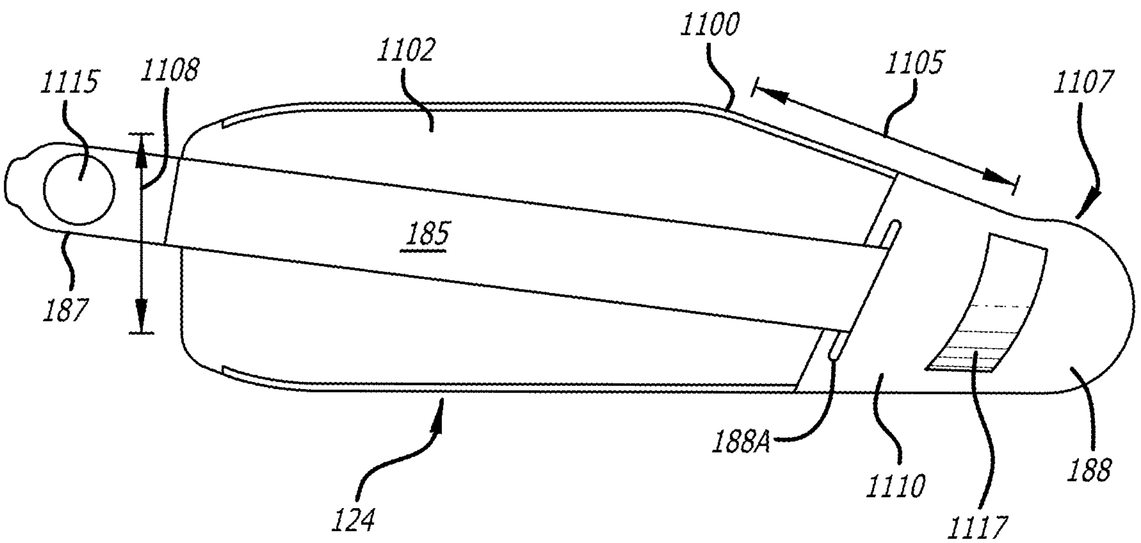
FIG. 11G is a view of a third embodiment of an outer (or posterior) side of a second belt arm 124 having a handling strap 1117 disposed thereon on according to an implementation of the disclosure.
Figure 11H:
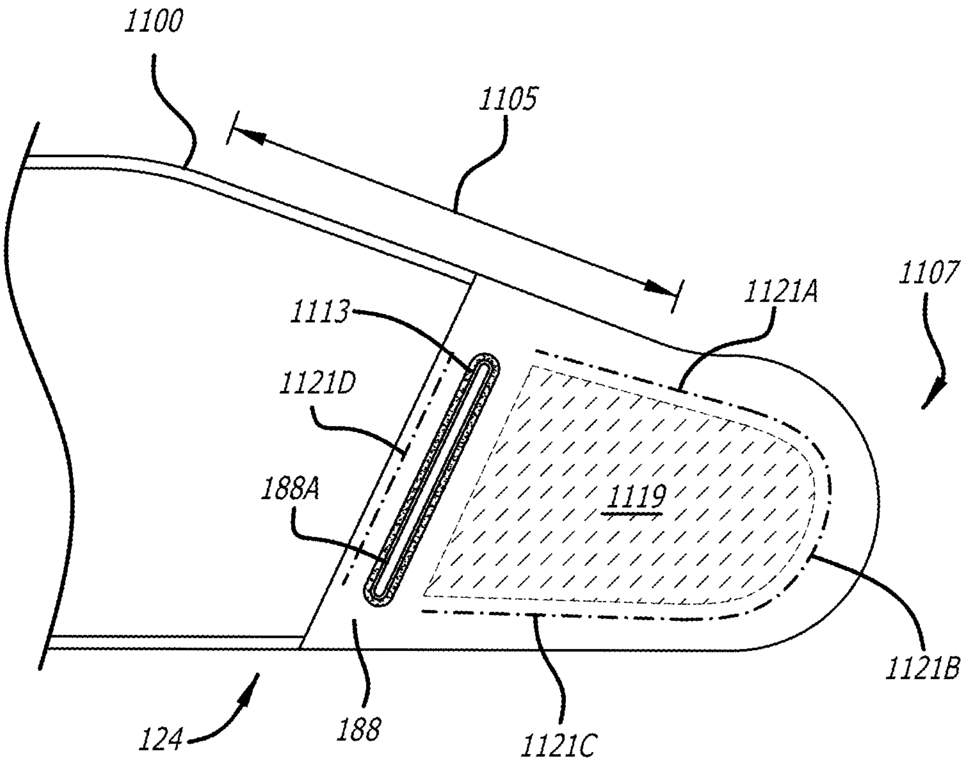
FIG. 11H is a detailed view of the distal end of the second belt arm 124 according to an implementation of the disclosure.
Figure 11I:
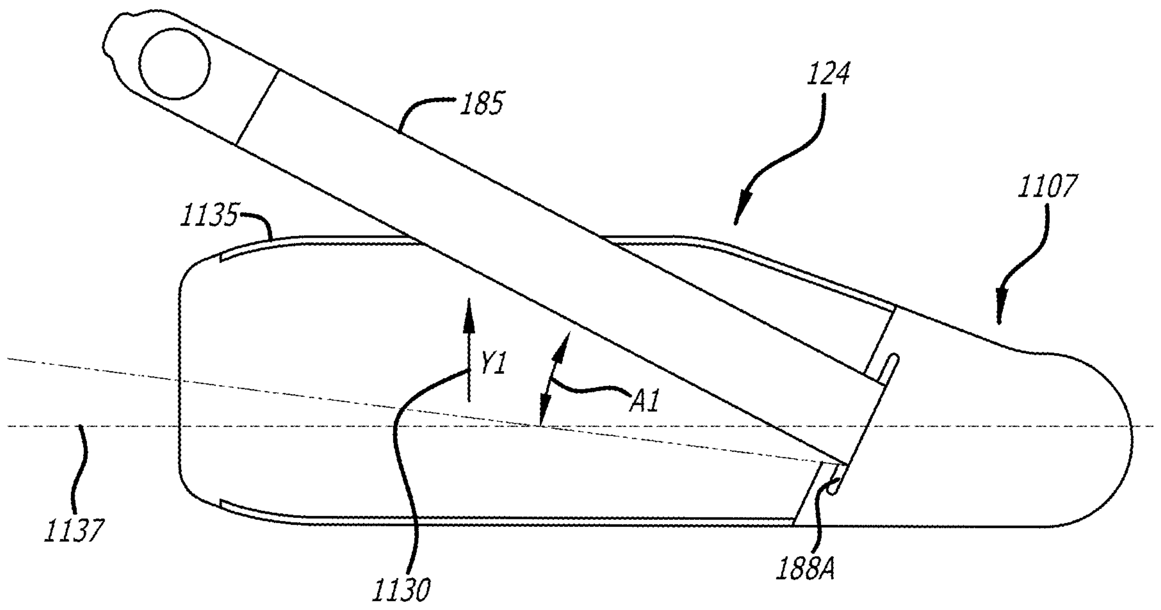
FIG. 11I illustrates the outer side of the second belt arm 124 with the second tightening strap 185 positioned at a first angle relative to a longitudinal axis according to an implementation of the disclosure.
Figure 11J:
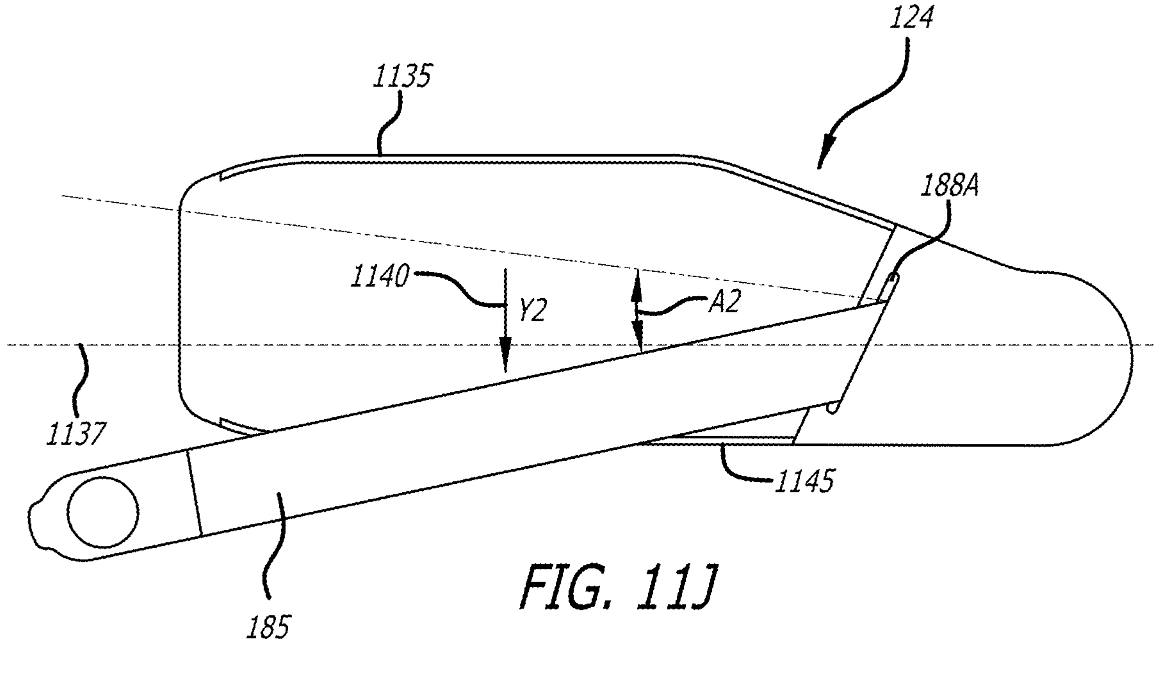
FIG. 11J illustrates the outer side of the second belt arm 124 with the second tightening strap 185 positioned at a second angle relative to the longitudinal axis according to an implementation of the disclosure.

As further shown in FIG. 10A, the outer side of the first belt arm 122 includes fasteners 1010 (e.g., hook fasteners) for attachment to an inner side of the second belt arm 124 as shown in FIG. 11J when the brace 100 of FIG. 1A is worn. Also, the first tightening strap 180 features a first (distal) end (not shown) inserted through slot 183A and attached to a strap anchoring member (see member 1120 of FIG. 11B), which is a durable material (e.g., elastic or semi-elastic material) located within an interior of the pocket 183 and directly or indirectly coupled to the fabric 1002 within the interior of the pocket 183 that provides lift when the first tightening strap 180 is tightened. The second end be of the first tightening strap 180 is inserted through the first slot 220 of the first tightening strap fastener 190 and folded over itself for attachment to an outer surface of the first tightening strap 180, which may feature UBL or other fastening mechanisms complementary to a posterior region of the second end 182 of the first tightening strap 180 and an aperture 1015 to allow the wearer to insert her/his digit (e.g., thumb) to tighten the brace (e.g., provide posterior compression and anterior lift).

According to this embodiment of the disclosure, the pocket 183 is elongated to allow the wearer to insert her or his hand (or multiple fingers of the wearer's left hand) through the slot 183A and into the pocket 183. This assists the wearer in placement of the first belt arm 122 under a protruding belly area for a pregnant wearer or a bariatric patient. The outer surface 184 of the pocket 183 may include UBL material (i.e., UBL fastener).

Figure 10B:
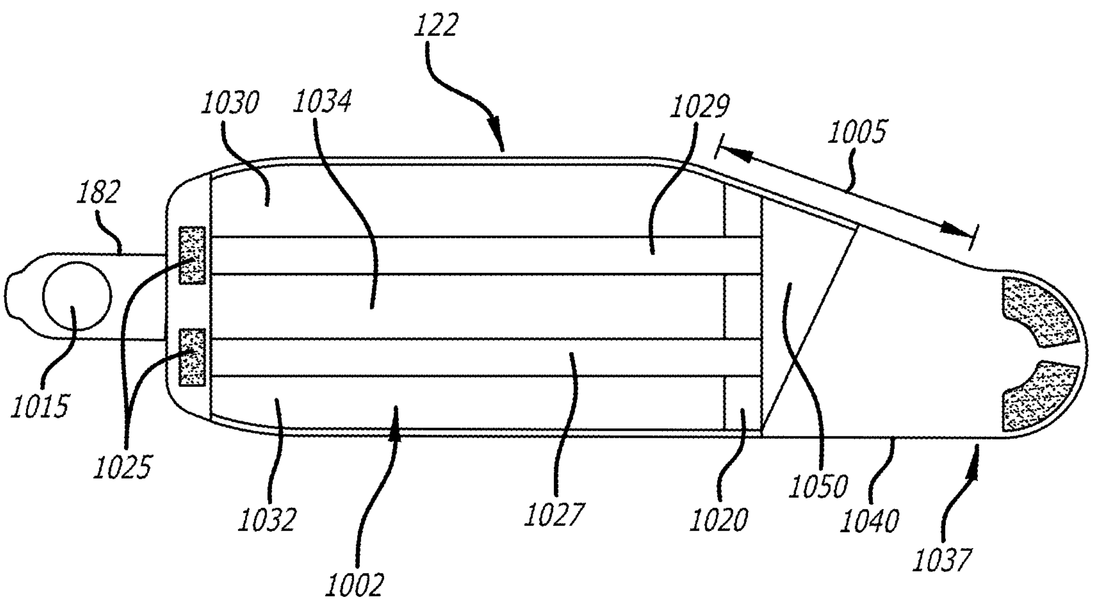
FIG. 10B is a view of an inner side of the first belt arm 122 coupled to the tightening mechanism 110 according to an implementation of the disclosure.

Referring to FIG. 10B, according to an implementation of the disclosure, an exemplary embodiment of an inner side of the first belt arm 122, which is coupled to the tightening mechanism 110 of FIG. 10A for example, is shown. The inner side features one or more columns of inelastic material (e.g., a first column of UBL materials 1020 and a second column of UBL material 1022), which are positioned towards the distal end 1007 of the first belt arm 122 and a proximal end of the first belt arm 122 that would be inserted through the first elongated slot 131 of the first belt pulley base 130. As shown, the second column of UBL material 1022 features one or more hook fasteners 1025 aligned with one or more rows of inelastic UBL material 1027 and 1029, respectively. It is contemplated that additional columns of UBL material may be positioned on the inner side of the first belt arm 122 to provide additional rigidity as the sizing (length) of the first belt arm 122 increases.

The inner side of the first belt arm 122 further features one or more rows of inelastic (UBL) material 1027 and 1029, which extend between the first and second columns of UBL material 1020 and 1022. The first and second rows of UBL material 1027 and 1029 are spaced equivalent to the spacing of the hook fasteners 1025 so that, when the proximal end of the first belt arm 122 is inserted through the first elongated slot 131 of the first belt pulley base 130, the proximal end including the second column of UBL material 1022 is folded and the hook fasteners 1025 are attached to the first and second rows of the UBL material 1027 and 1029.

Herein, the one or more columns with inelastic material 1020 and 1022 (e.g., UBL material) are positioned to substantially mitigate the elasticity of the first belt arm 122 generally in the transverse plane direction (X-axis), given that the fabric 1002 is elastic. Additionally, the one or more rows of inelastic material 1027 and 1029 are positioned to substantially mitigate the elasticity of the first belt arm 122 generally in the sagittal plane direction (Y-axis). As a result, segments of the fabric 1002, namely a first segment of fabric 1030 and a second segment of fabric 1032 positioned proximate to the reinforced edge 1000, allow for elasticity around a Z-axis. A third segment of fabric 1034 provides elasticity for increased flexibility against a side of the wearer.

A distal end 1037 of the inner side of the first belt arm 122 features inelastic material such as an optional UBL fastener

1040. Based on this construction, an expansion region 1050 is interposed between the UBL fastener 1040 and the first column of inelastic material 1020. The expansion region 1050 as illustrated in greater detail in FIG. 10C.

Figure 10C:
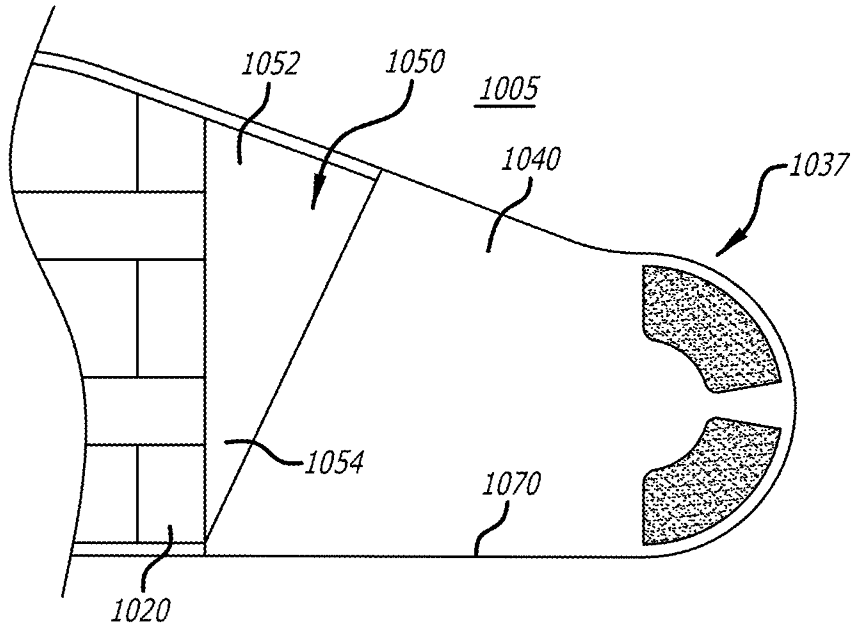
FIG. 10C is a detailed view of a distal end of the inner side of the first belt arm 122 according to an implementation of the disclosure.

Referring to FIG. 10C, a detailed view of the distal end 1037 of the inner side of the first belt arm 122 is shown according to an implementation of the disclosure. The expansion region 1050 is interposed between the UBL fastener 1040 (inelastic material) and the first column of inelastic material 1020. Herein, the expansion region 1050 is sized with a first width 1052 adjacent to the reinforced edge segment that is greater than the remaining widths within the expansion region 1050, such as a second width 1054 aligned with the first row of inelastic (UBL) material 1027. This construction is intended so as to provide greater elasticity (and stretch) near the apex of the extended belly and lesser elasticity toward a bottom edge 1070 that is positioned under the extended belly of the wearer and configured to provide lift upon tightening of the brace 100 through the first tightening strap 180 of FIGS. 10A-10B. In some embodiments, the expansion region 1050 has a triangular shape. In other embodiments, the expansion region 1050 has a trapezoidal shape. Other geometric shapes or forms have also been contemplated.

Referring to FIG. 11A, a view of an outer (or posterior) side of a second belt arm 124 is shown according to an implementation of the disclosure. Herein, the second belt arm 124 features a reinforced edge 1100 that circumvents a breathable semi-elastic fabric 1102 forming the second belt arm 124. A segment 1105 of the second belt arm 124 is provided with a downward slope, generally equivalent to the downward slope of the first belt arm 122, so that a distal end 1107 of the second belt arm 124, which featuring a portion of the pocket 188, has a width that ranges between ¼ and ¾ of the width of a proximal end 1108 of the second belt arm 124. The segment 1105 may be referred to as a tapered portion with a tapering toward a distal end of the second belt arm 124.

As further shown in FIG. 11A, the outer side of the second belt arm 124 includes an inelastic material 1110 (e.g., UBL material) that is outfacing when the brace 100 of FIG. 1A is worn. Also, the second tightening strap 185 features a first (distal) end (not shown) inserted through slot 188A and attached to a strap anchoring member (see strap anchoring member 1120 of FIG. 11B), which is a durable material (e.g., semi-elastic material) located within an interior of the pocket 188 and directly or indirectly coupled to the fabric 1102 within the interior of the pocket 188 that provides lift when the second tightening strap 185 is tightened. The second end 187 of the second tightening strap 185 may feature a hook fastener or other fastening mechanisms complementary to an outer surface of the second end 187 of the tightening strap 185 and an aperture 1115 to allow the wearer to insert her/his digit to tighten the brace (e.g., provide posterior compression and anterior lift).

Two embodiments of the second tightening strap 185 are illustrated in FIGS. 11B-11C and discussed below. It should be understood that either embodiment (and their respective connection mechanisms to the interior of the pocket 188 may be utilized) in any embodiment discussed throughout this disclosure. During discussion of the first embodiment, the second tightening strap 185 is referred to as the second tightening strap 185A. Similarly, during discussion of the second embodiment, the second tightening strap 185 is referred to as the second tightening strap 185B. The remainder of the disclosure utilizes the term "the second tightening strap 185," which should be understood to refer to either embodiment. Finally, it should be understood that the two embodiments of the second tightening strap 185 similarly apply to the first tightening strap 180.

Referring to FIG. 11B, a view of a first embodiment of the outer side of the second belt arm 124 is shown according to an implementation of the disclosure. Specifically, the first embodiment of FIG. 11B illustrates the second belt arm 124 including an elastic strap anchoring member 1120 disposed within a distal, elongated pocket 188. Herein, the anchoring member 1120 may feature one or more anchors, such as a plurality of anchors 1122 and 1124 attached to the fabric 1102 within an interior of the pocket 188. The term "attached to" may refer a fixture such as sewing, adhesive, welding, etc. Hence, as the anchoring member 1120 is coupled to the first (distal) end 186 of the second tightening strap 185A and a proximal end of the second tightening strap 185A is coupled to the second tightening strap fastener 195 (see FIG. 5), the distal pulling of the second tightening strap 185A causes lift forces to be felt under the extended belly of the wearer and compression to be felt on a lower back of the wearer, respectively. As shown, the anchors 1122 and 1124 create an overlay area and may be positioned in a V-shaped arrangement, although other arrangements may be utilized.

Referring to now FIG. 11C, a view of a second embodiment of the outer side of the second belt arm 124 is shown according to an implementation of the disclosure. Specifically, the second embodiment of FIG. 11C illustrates the second belt arm 124 including a connector ring 1128A coupled to an interior of the pocket 188 through an elastic strap 1126 (where the connector ring 1128A and the elastic strap 1126 may be referred to an anchoring member). The elastic strap 1126 may be sewn to the interior of the pocket 188, may be welded thereto, or may be otherwise coupled thereto such as through an adhesive. In the embodiment of FIG. 11B, the second tightening strap 185A is sewn (or welded) to the anchoring member 1120, which is sewn (or welded) to the interior of the pocket 188. In such an embodiment, the second tightening strap 185A is permanently affixed to the anchoring member 1120, which is permanently affixed to the interior of the pocket 188. As a result, the length of the second tightening strap 185A as measured from the anchoring member 1120 to the proximal end of the second tightening strap 185A opposite the anchoring member 1120 is static.

In contrast, the embodiment of FIG. 11C enables adjustment of the length of the second tightening strap 185B as measured from the connector ring 1128A to the proximal end of the second tightening strap 185B opposite the connector ring 1128A as discussed in detail with respect to FIG. 11D. Both embodiments illustrated in FIGS. 11B-11C enable movement of the second tightening strap 185 relative to a longitudinal axis as described with respect to FIGS. 11G-11H.

Referring now to FIG. 11D, a detailed view of the distal end of the second belt arm 124 depicting the second embodiment of FIG. 11C is shown according to an implementation of the disclosure. As noted above, the second embodiment of the second belt arm 124 includes the second tightening strap 185B that is removably coupled to the connector ring 1128A. Specifically, a first end 1129A of the second tightening strap 185B has been threaded through an elongated slot 1128B of the connector ring 1128A and folded over onto itself such that a fastening element 1129B positioned at the first end 1129A couples with the material (e.g., UBL) of the second tightening strap 185B itself. The positioning of the coupling may vary depending on how the second tightening strap 185B is initially sized. For example, the second tightening strap 185B may be sized for a smaller circumference by positioning the coupling of the fastening 1129B in a more proximal position (e.g., away from the connector ring 1128A) with the positioning of the coupling of the second end 187 onto the tightening strap 185 itself providing more of a tailored and precise adjustment of the fitting of the brace 100 compared to the coarse adjustment provided by the positioning of the a fastening element 1129B along the length of the second tightening strap 185B. By decreasing the length of the second tightening strap 185B as measured between the connector ring 1128A and the proximal end of the second tightening strap 185B (opposite the connector ring 1128A), the user (wearer) increases the leverage the user has to tighten the brace 100.

Referring to FIG. 11E, a view of an outer (or posterior) side of a second belt arm 124 having an additional, secondary exterior pocket 1111 is shown according to an implementation of the disclosure. Herein, the second belt arm 124 features a secondary exterior pocket 1111 that may be coupled to the exterior side of the pocket 188 and be configured to receive a hand of a user or portion thereof. The exterior pocket 1111 provides the user an alternative to placing their hand or portion thereof in the opening 188A of the pocket 188. As a result, movement of the second tightening strap 185 is unencumbered during donning of the brace 100.

Referring to FIG. 11F, a view of a second embodiment of an outer (or posterior) side of a second belt arm 124 having a reinforced edging 1113 around a slot 188A in a pocket 188 of the belt arm 124 is shown according to an implementation of the disclosure. Herein, the second belt arm 124 features reinforced edging 1113 around the slot 188A of the pocket 188. The reinforced edging 1113 may be injected or molded in place (e.g., "overmolded") or formed as a coating, heat seal, or laminated film. The reinforced edging 1113 may be formed of a plastic or elastomeric material (polyvinyl chloride, thermoplastic polyurethane, thermoplastic elastomer, polyethylene/polypropylene, silicone rubber, etc.) or may be formed of a textile-based material such as polyester, nylon, cotton, bias or twill tape, corded or piped edging, etc.). As a result of the reinforced edging 1113, the slot 188A may be configured to receive a hand of a user or portion thereof and be better equipped to avoid tears or an undesired expansion of the slot 188A as the user inserts a hand or portion thereof into the slot 188A during donning of the brace 100. Additionally, a similar reinforced edging 1115A is seen as an optional feature surrounding the aperture 1115 in the tightening strap 185.

Referring to FIG. 11G, a view of a third embodiment of an outer (or posterior) side of a second belt arm 124 having a handling strap 1117 disposed thereon on is shown according to an implementation of the disclosure. Herein, the second belt arm 124 features the handling strap 1117 that may be coupled to the exterior side of the pocket 188 and be configured to receive a hand of a user or portion thereof. The handling strap 1117 provides the user an alternative to placing their hand or portion thereof in the opening 188A of the pocket 188. As a result, movement of the second tightening strap 185 is unencumbered during donning of the brace 100.

Referring to now FIG. 11H, a detailed view of the distal end of the second belt arm 124 is shown according to an implementation of the disclosure. FIG. 11H illustrates that in some embodiments, the pocket 188 may include an insert 1119, e.g., formed of plastic, that is configured to prevent the distal end of the second belt arm 124 from collapsing or scrunching during the donning process or while being worn. The insert 1119 provides stability and compliance to ensure the brace 100 provides adequate support and tightness. In some examples, the insert 1119 is maintained in place through closure strips 1121A-1121D, which may be, for example, welding strips or sewing strips.

Referring to FIG. 11I, the outer side of the second belt arm 124 with the second tightening strap 185 positioned at a first angle (A1) relative to a central longitudinal axis 1137 is shown according to an implementation of the disclosure. Herein, the first angle A1 may range up to 45 degrees to allow for the wearer to pull upward (generally in a Y1-direction) 1130 on the tightening strap 185 to apply lifting forces at or near the distal end 1107 of the second belt arm 124. Similarly, as shown in FIG. 11J, the second tightening strap 185 may be oriented at a second angle (A2) relative to the central longitudinal axis 1137 (where angle $A2 \leq -45°$) to allow for the wearer to pull downward (generally in a Y2-direction) 1140 on the tightening strap 185 towards a bottom edge 1145 of the second belt arm 124 to apply lifting forces at or near the distal end 1107 of the second belt arm 124 along with the compression by the tightening mechanism 110 located proximate to the lower back of the wearer.

Figure 11K:
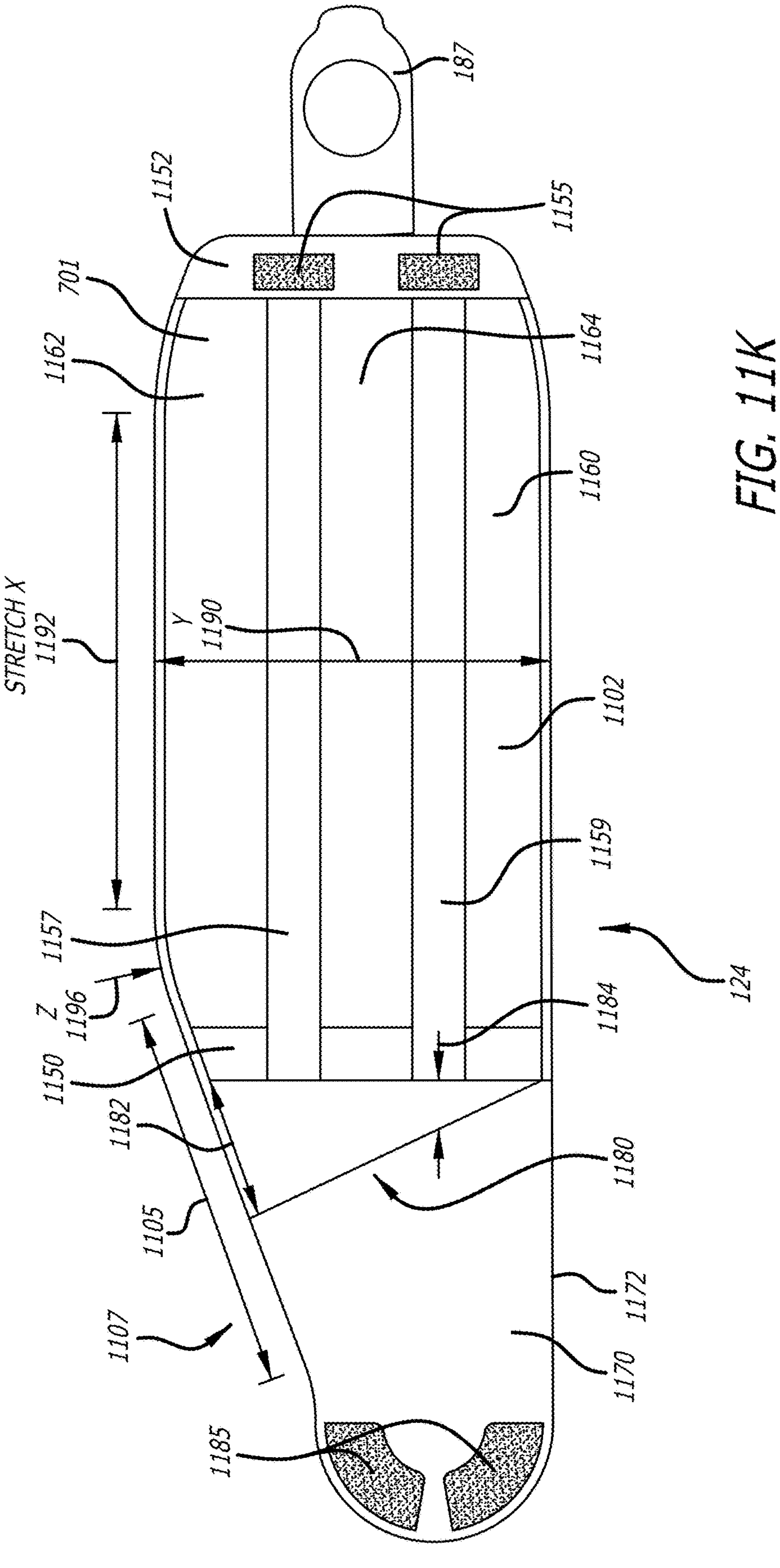
FIG. 11K is a view of an inner side of the second belt arm 124 according to an implementation of the disclosure.

Referring to FIG. 11K, a view of an inner (or anterior) side of the second belt arm 124 is shown according to an implementation of the disclosure. Herein, the inner side of the second belt arm 124 features one or more columns of inelastic material (e.g., a first column of UBL material 1150 and a second column of UBL material 1152), which are positioned towards the distal end 1107 of the second belt arm 124 and a proximal end of the second belt arm 124, which would be inserted through the first elongated slot 141 of the second belt pulley base 140 as shown in FIG. 1C2. Additionally, the second column of UBL material 1152 features one or more hook fasteners 1155 aligned with one or more rows of inelastic (UBL) material 1157 and 1159, respectively.

As further shown in FIG. 11K, the inner side of the second belt arm 124 features one or more rows of inelastic (UBL) material 1157 and 1159, which extend between the first and second columns of UBL materials 1150 and 1152. The first and second rows of UBL material 1157 and 1159 are spaced equivalent to the spacing of the hook fasteners 1155 so that, when the proximal end of the second belt arm 124 is inserted through the first elongated slot 141 of the second belt pulley base 140 as shown in FIG. 1C2, the proximal end 1108 including the second UBL column 1152 would be folded and the hook fasteners 1155 would attach to the first and second rows of the UBL material 1157 and 1159.

Herein, similar to FIG. 10C illustrating the first belt arm 122, the one or more columns of inelastic material 1150 and 1152 (e.g., UBL material) are positioned to substantially mitigate the elasticity of the second belt arm 124 generally in the sagittal plane direction (Y-axis 1190), given that the fabric 1102 is elastic. Additionally, the one or more rows of inelastic material 1157 and 1159 are positioned to substantially mitigate the elasticity of the second belt arm 124 generally in the transverse plane direction (X-axis 1192). As a result, segments of the fabric 1102, namely a first segment of fabric 1160 and a second segment of fabric 1162 positioned proximate to the reinforced edged, allow for elasticity around a Z-axis 1196. A third segment of fabric 1164 provides elasticity for increased flexibility against a side of the wearer.

A distal end 1107 of the second belt arm 124 features a UBL fastener 1170, which is complementary to one or more hook fasteners positioned on an outer side of the first belt arm 122 as shown in FIG. 10A. The inner surface of the second belt arm 124 further features one or more hook fasteners 1185 for attachment to the UBL fastener 184 located on the outer surface of the pocket 183 of the first belt arm 122. Based on this construction, an expansion region 1180 is interposed between the UBL fastener 1170 and the first column of inelastic material 1150.

As shown in FIG. 11K, the expansion region 1180 is sized with a first width 1182 (adjacent to the reinforced edge segment 1105) is greater than the remaining widths within the expansion region 1180 such as a second width 1184 aligned with the second row of inelastic (UBL) material 1159. This construction is intended so as to provide greater elasticity (and stretch) near the apex of the extended belly when the distal end 1107 of the second belt arm 124 is positioned over the distal end 1007 of the first belt arm 122 during the donning process (see FIGS. 13A-13E) and lesser elasticity toward a bottom edge 1172 that is positioned under the extended belly of the wearer and configured to provide lift upon tightening of the brace 100.

Figure 12:
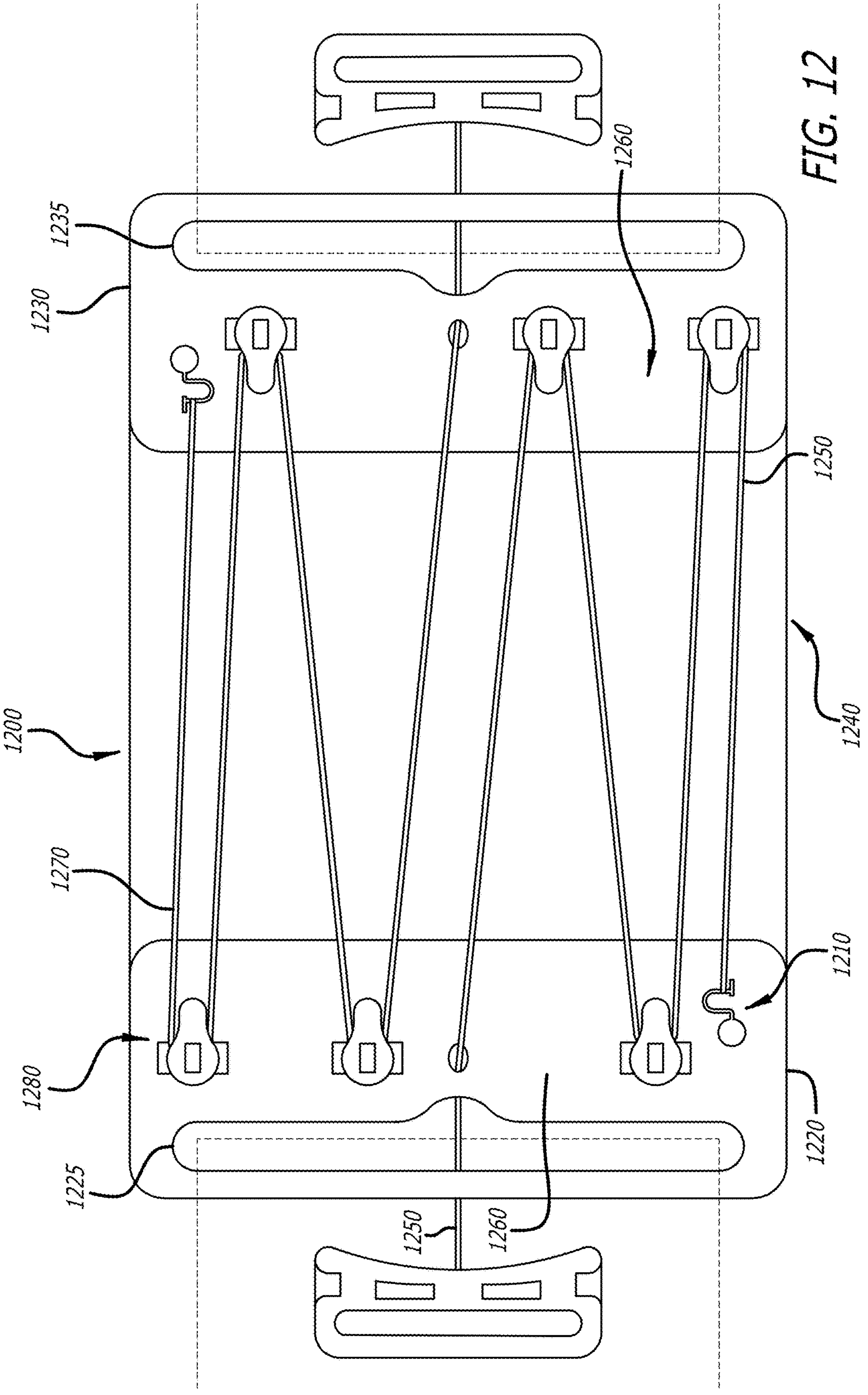
FIG. 12 is a view of an outer side of a second tightening mechanism 1200 that may be utilized in conjunction with the first and second belt arms 122, 124 according to an implementation of the disclosure.

Referring to FIG. 12, a view of an outer side of a second tightening mechanism 1200 that may be utilized in conjunction with the first and second belt arms 122, 124 is shown according to an implementation of the disclosure. Herein, the second tightening mechanism 1200 includes a pulley system 1210 with a 4:1 mechanical advantage. According to this embodiment, the pulley system 1210 includes a first pulley base 1220, a second pulley base 1230 and a mesh interconnect 1240 attached to the first pulley base 1220 and the second pulley base 1230. A first cord segment 1250 is interchanged between a first set of pulleys 1260 located in lower regions of the first pulley base 1220 and the second pulley base 1230. Also, a second cord segment 1270 is interchanged between a second set of pulleys 1280 located in upper regions of the first pulley base 1220 and the second pulley base 1230. It is contemplated that the first and second belt arms 122 and 124 may be utilized with tightening mechanisms with different pulley configuration than the first tightening mechanism 110 and the second tightening mechanism 1200.

As shown in FIG. 12, the first belt arm 122 is attached to a first connector 1225 of the first pulley base 1220, and the second belt arm 124 is attached to a second connector 1235 of the second pulley base 1230. Hence, after wrapping the first and second belt arms 122 and 124 around the wearer, the first and second cord segments 1250 and 1270 may be pulled to cause lateral movement of the first and second pulley bases 1220 and 1230 to converge.

Figure 13A:
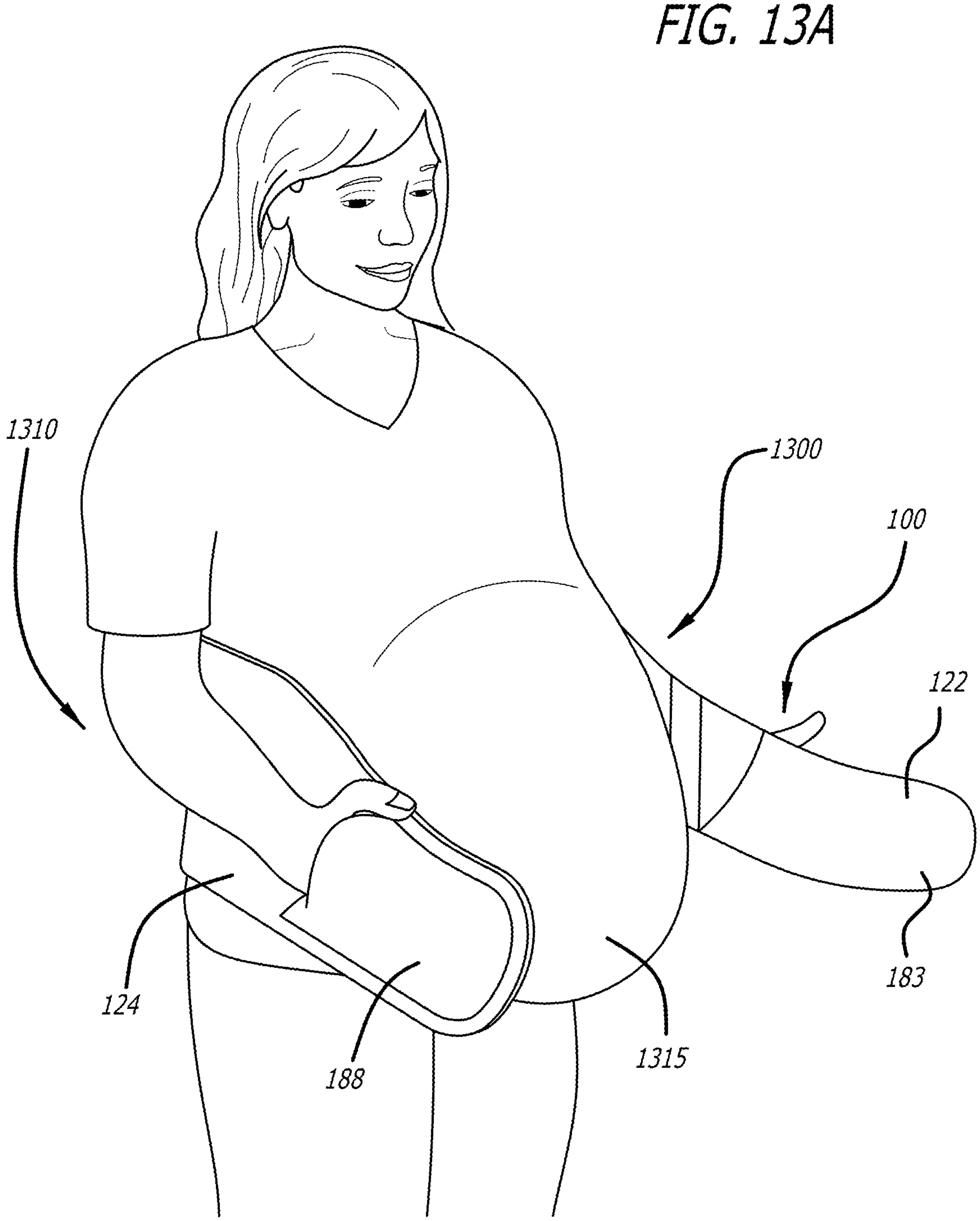
FIGS. 13A-13F illustrate a series of steps in donning an embodiment of the brace 100 according to an implementation of the disclosure.

Referring to FIGS. 13A-13F, a series of steps in donning an embodiment of the brace 100 is shown according to an implementation of the disclosure. As shown in FIG. 13A, the brace 100 is placed on the wearer1300 with the first and second belt arms 122 and 124 extending from the left and right sides of the wearer 1300 (operation 1310), The pocket 183 of the first belt arm 122 and the pocket 188 of the second belt arm 124 feature an elongated size to receive a portion of the wearer's hand (e.g., fingers excluding thumb) for easy movability of the distal ends of the belt arms 122 and 124.

Figure 13B:
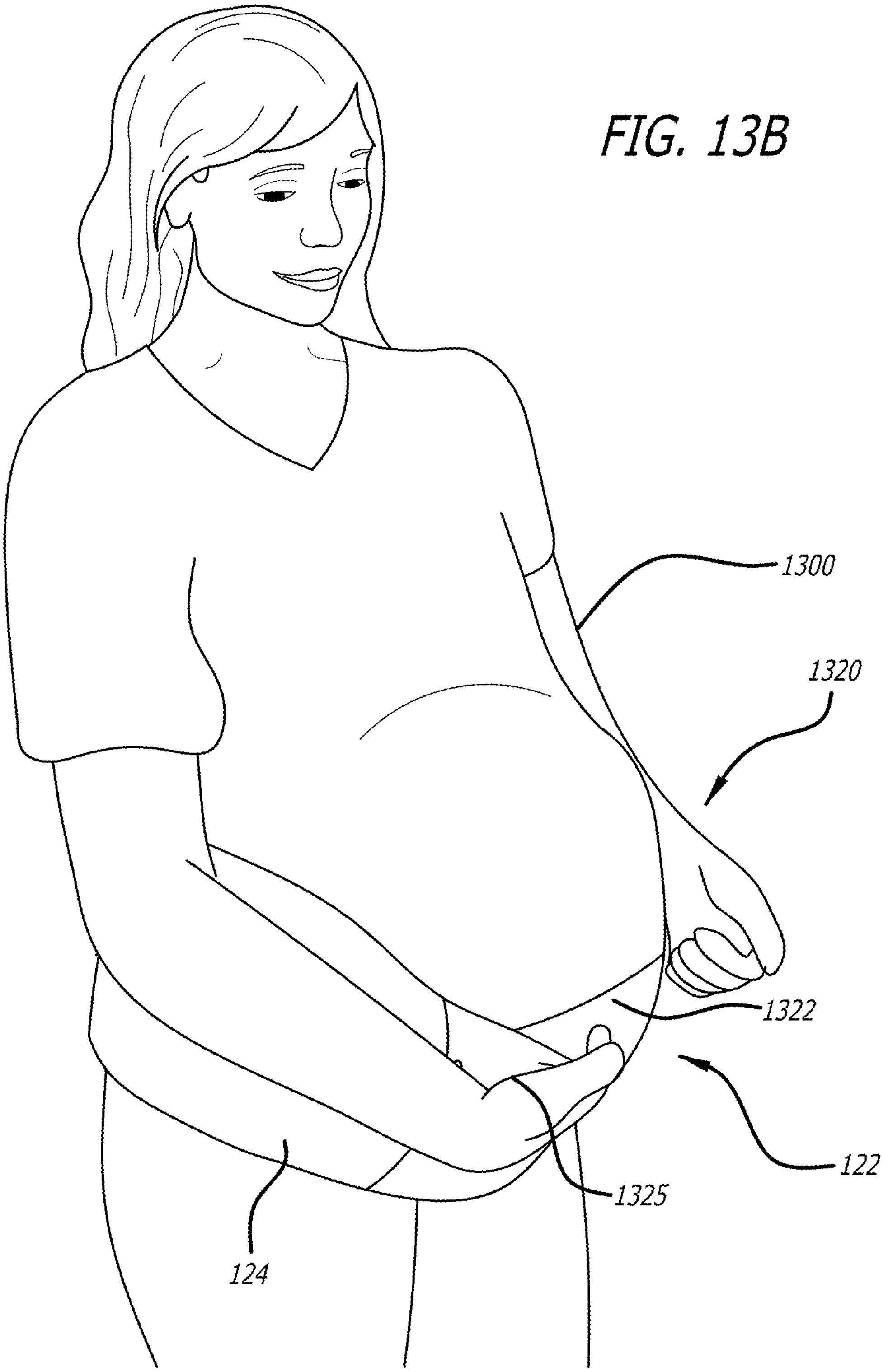

As shown in FIG. 13B, the distal end of the first belt arm 122 is positioned under and against an extended abdomen region 1322 of the wearer 1300, followed by a distal end 1325 of the second belt arm 124 being positioned over the distal end of the first belt arm 122 (operation 1320). As a result, hook fasteners 1010 located on an outer side of the first belt arm 122 (see FIG. 10A) attached to the UBL fastener 1170 located on the inner side of the second belt arm 124 (see FIG. 11E). Also, the hook fasteners 1185 located on the inner side of the second belt arm 124 (see FIG. 11E) attaches to the outer UBL fastener 1040 of the first belt arm 122 (see FIG. 10C).

Figure 13C:
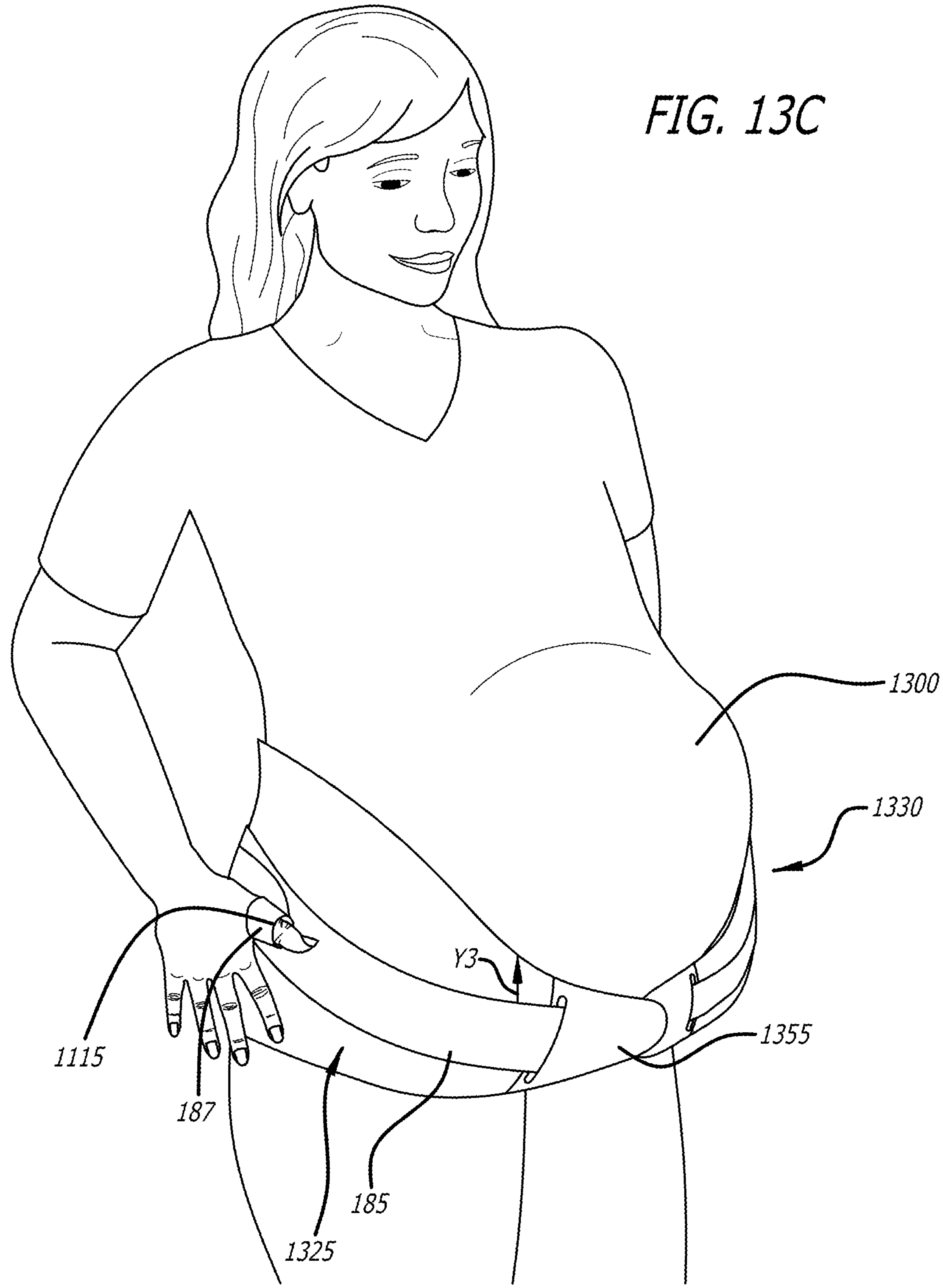
Figure 13D:
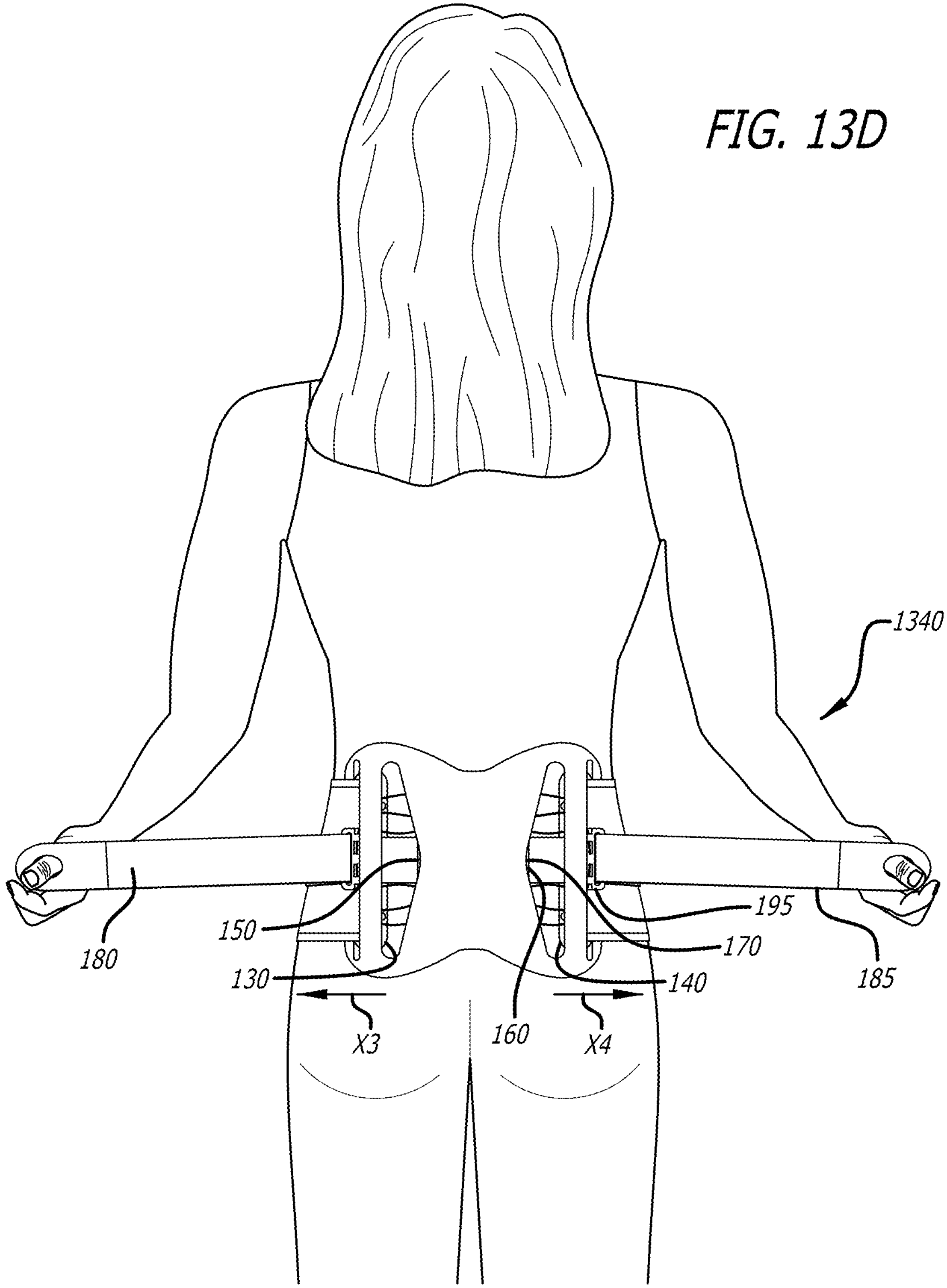
Figure 13E:
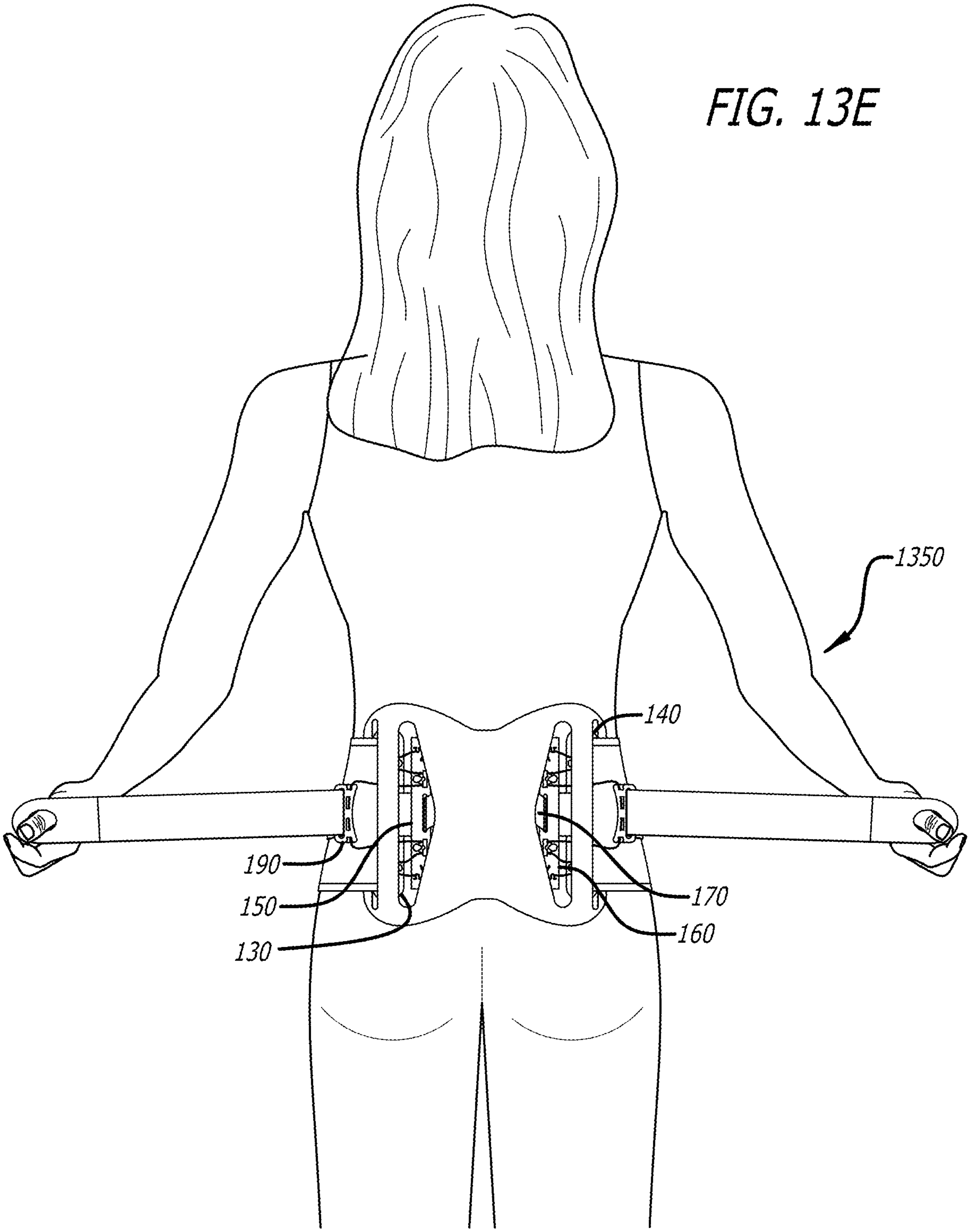

Therefore, as illustrated in FIGS. 13C-13E, the wearer 1300 grabs the second ends 182 and 187 of the tightening straps 180 and 185 (e.g., apertures 1015 and 1115) and applies forces to move the ends within the frontal plane toward from the wearer 1300 to concurrently apply forces to the strap anchoring members attached to the distal ends of the tightening straps 180 and 185 (coupled to the distal ends of the belt arms) and the tightening strap fasteners 190 and 195 attached to the strap pulley bases 150 and 160 and belt pulley bases 130 and 140 via cord segments 175 and 177, respectively (operations 1330, 1340 and 1350). More specifically, when the tightening straps 180 and 185 are pulled in a distal direction generally forward and away from the wearer 1300, the anchoring members (e.g., first strap anchoring member and second strap anchoring member 1120 shown in FIG. 11B) are stretched to apply a generally upward force (lift) under the extended abdomen. Concurrently, the tightening strap fasteners 190 and 195 are pulled by the tightening straps 180 and 185 laterally, which causes lateral movement of the first and second strap pulley bases 150 and 160 and elongation (stretching) of the elastic strapping 170. This provides compression against a lower back of the wearer 1300.

Figure 13F:
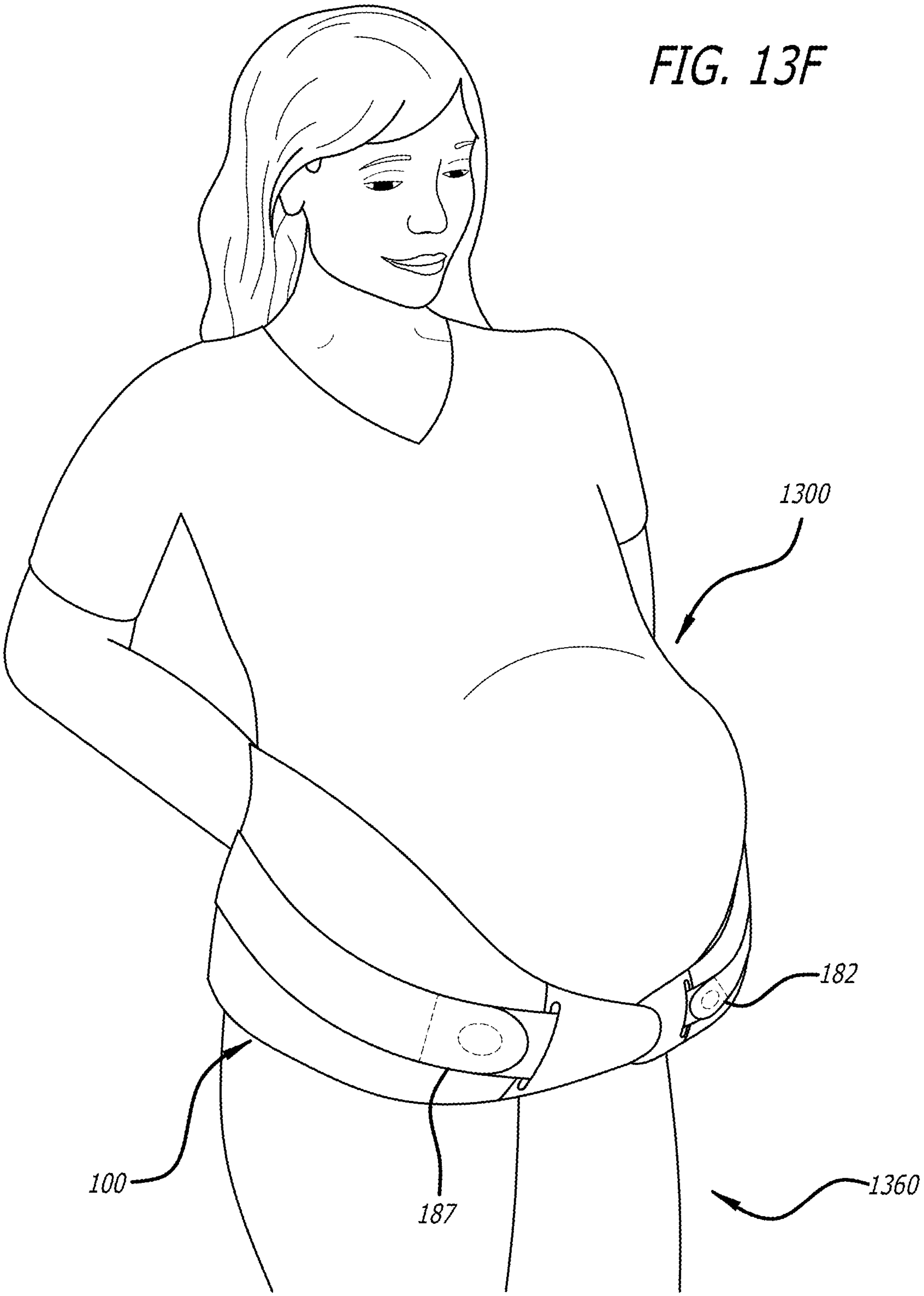

As shown in FIG. 13F, once the tightening straps 180 and 185 of the brace 100 are adjusted to provide sufficient lift of the abdomen region (extended belly) and compression against the lower back of the wearer 1300, the second ends 182 and 187 of the first and second tightening straps 180 and 185 are attached to these straps 180 and 185 (operation 1360). The seconds ends 182 and 187 could also be attached onto the outer UBL surfaces of the pockets 183 And 188 This may be accomplished by the outer regions of the second ends 182 and 187 having a fastener complementary to a fastener positioned on the inner surface (or the composition material) of the tightening straps 180 and 185.

Figure 14A:
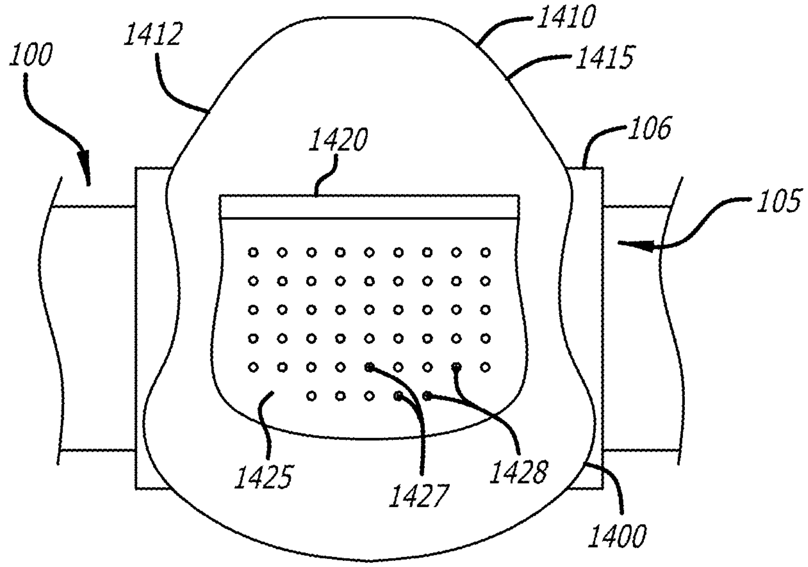
FIG. 14A is an anterior view of a removably attachable back panel according to an implementation of the disclosure.

Referring to FIG. 14A, an inner view of a removably attachable back panel 1410 attached to the inner layer 106 of the padded posterior sleeve 105 of the brace 100 is shown according to an implementation of the disclosure. When a posterior of the back panel 1410 is attached to the padded posterior sleeve 105, a top region 1412 of the back panel 1410 extends above the sleeve to support a thoracic region of the wearer, and thus, the brace 100 may be construed as a type of lumbar-sacral orthosis (LSO).

As shown, according to one embodiment of the disclosure, an inner surface 1415 of the back panel 1410 features a pocket (enclosure) 1420 configured to receive a hot/cold therapy pack in lieu of the internal pocket 105B located on the padded posterior sleeve 105. An inner surface 1425 of the pocket 1420 may feature recesses 1427-1428 of different depths and/or diameters to reduce the amount of installation between the hot/cold therapy pack (when inserted) and the back of the wearer. The recesses 1427-1428 provide heat/cooling to the wearer.

Figure 14B:
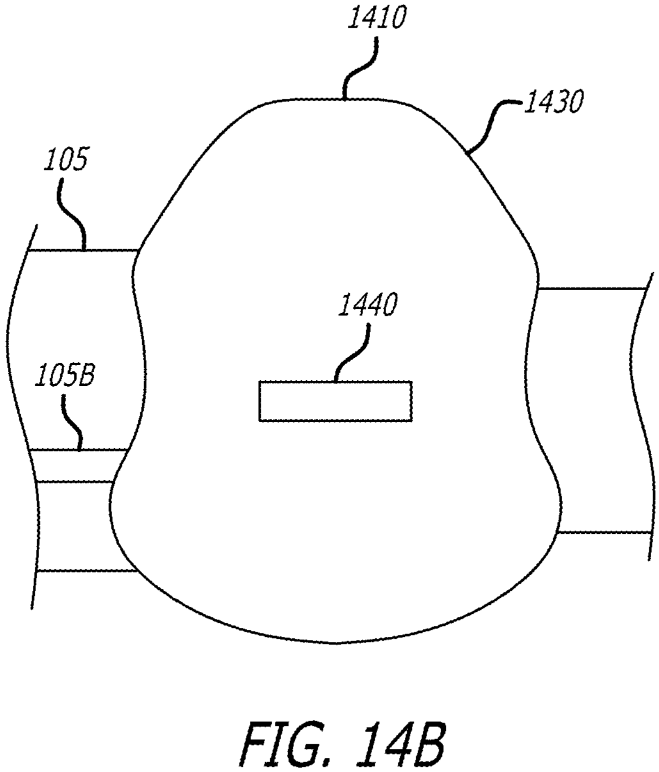
FIG. 14B is a posterior view of the removably attachable back panel of FIG. 14A according to an implementation of the disclosure.

Referring to FIG. 14B, a posterior (or outside/outward) view of the removably attachable back panel 1410 of FIG. 14A is shown according to an implementation of the disclosure. Herein, an outer surface 1430 of the back panel 1410 features a fastener 1440 for attachment to the padded posterior sleeve 105. For example, the internal pocket 105B of the posterior sleeve, a fastener (e.g., UBL material) complementary to the fastener 1440 (e.g., hook fastener) may be provided to allow the back panel 1410 to be secured to the padded posterior sleeve 105.

Figure 15A:
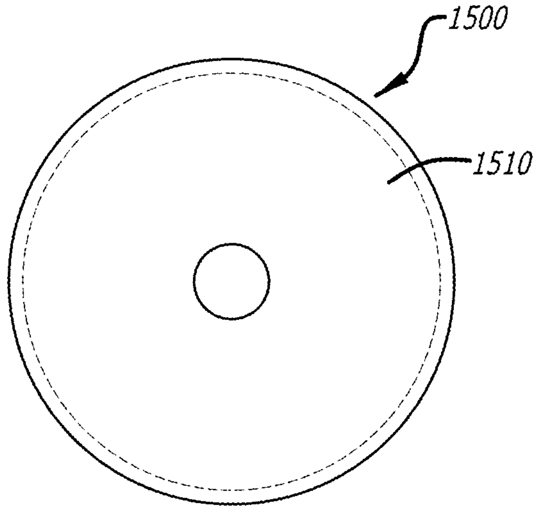
FIG. 15A is an anterior view of a removably attachable front torso panel according to an implementation of the disclosure.
Figure 15B:
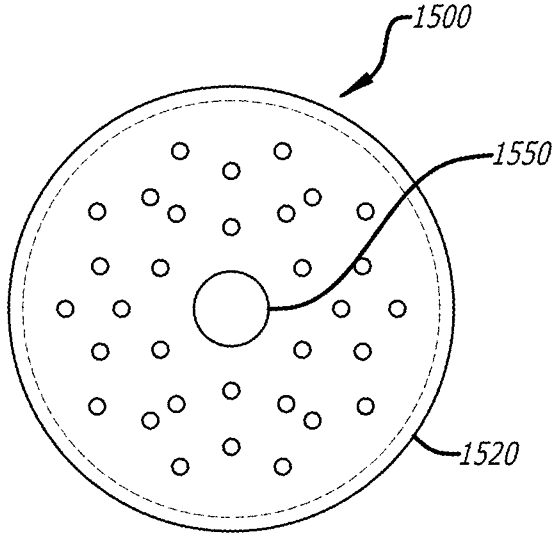
FIG. 15B is a posterior view of the removably attachable front torso panel of FIG. 15A according to an implementation of the disclosure.

Referring to FIG. 15A, an anterior (or inside/inward) view of a removably attachable anterior panel 1500 is shown according to an implementation of the disclosure. Herein, the anterior panel 1500 may be configured with a shape (e.g., circular, elliptical, rectangular etc.) to rest against the abdomen region of the wear when the LSO-style brace is worn. The anterior panel 1500 features an inner surface 1510 for placement against the abdomen region of the wear and an outer surface 1520 as shown in FIG. 15B. The outer surface 1520 of the anterior panel 1500, when installed, would be interposed between the inner surface of a corresponding belt arm 122 or 124. A fastener 1530 is positioned on the outer surface 1520 of the anterior panel 1500 for attachment to a complementary fastener (e.g., UBL fastener 1040 or UBL fastener 1170) positioned on a distal end of the first belt arm 122 as shown in FIG. 16A.

Figure 16A:
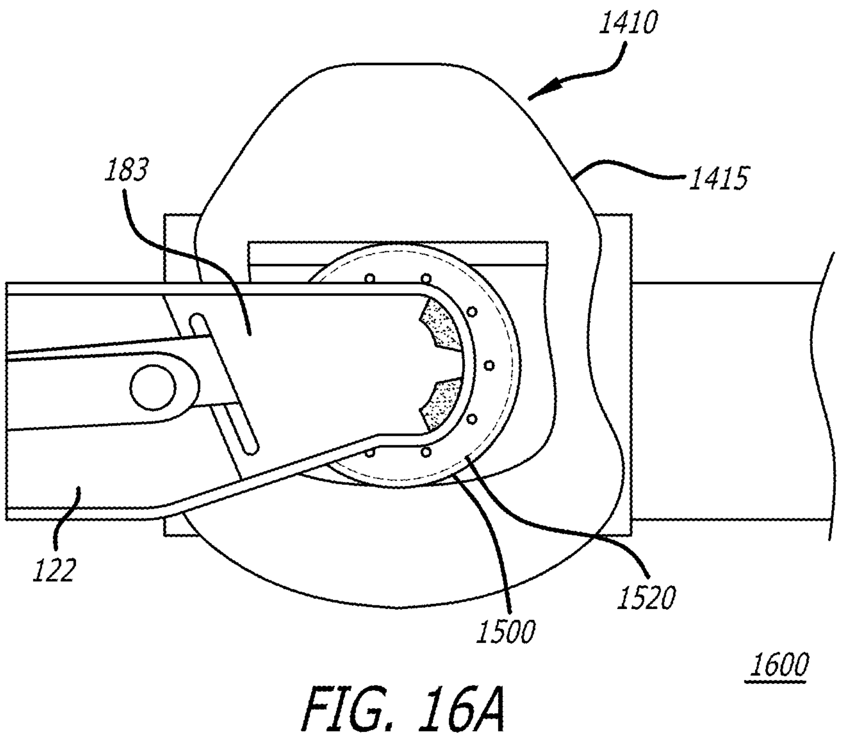
FIG. 16A is a first frontal posterior view of the removably attachable back panel of FIGS. 14A-14B and the removably attachable front torso panel of FIGS. 15A-15B each attached to the brace 100 according to an implementation of the disclosure.

Referring to FIG. 16A, according to an implementation of the disclosure, a first inner view of the removably attachable back panel 1410 of FIGS. 14A-14B and the removably attachable anterior panel 1500 of FIGS. 15A-15B each attached to the brace 100 to form an LSO variation 1600 is shown. The anterior panel 1500 is attached to a distal, inner region of the first belt arm 122 opposite to the pocket 183. As shown, the first belt arm 122 to folded so that the anterior panel 1500 is positioned anterior to and over the back panel 1410.

Figure 16B:
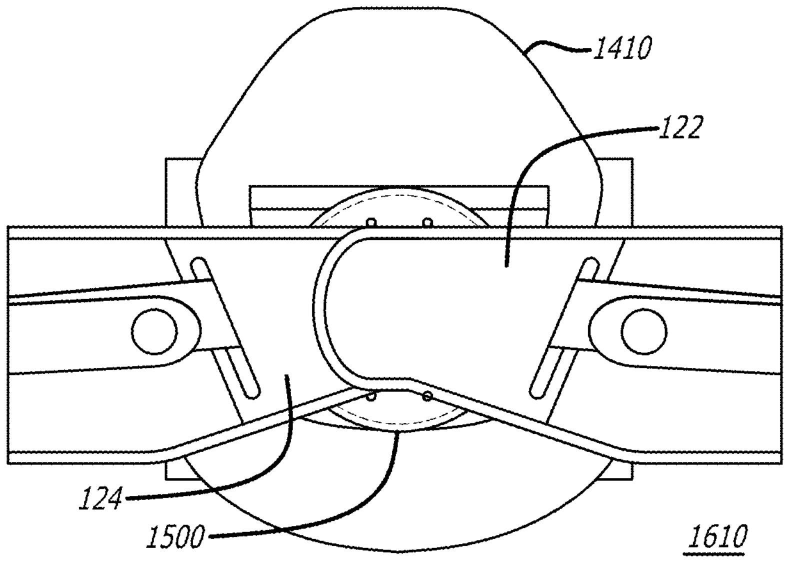
FIG. 16B is a second frontal anterior view of the removably attachable back panel of FIGS. 14A-14B and the removably attachable front torso panel of FIGS. 15A-15B each attached to the brace 100 according to an implementation of the disclosure.

Referring to FIG. 16B, according to an implementation of the disclosure, a second frontal posterior view of the removably attachable back panel of FIGS. 14A-14B and the removably attachable anterior panel 1500 of FIGS. 15A-15B is shown. Herein, the LSO variation 1610 is represented in a different mode of operation, where the first belt arm 122 is folded to position itself adjacent to the wearer while the second belt arm 124 is attached to the outer surface of the first belt arm 122 in the same manner as described above.

In the foregoing description, the invention is described with reference to specific exemplary embodiments thereof. Hence, it will be evident that certain components may be deployed within different types of orthopedic braces and various modifications and changes may be made thereto without departing from the broader spirit and scope of the invention as set forth in the appended claims.

What is claimed is:

1. An orthotic brace comprising:

a tightening mechanism including a pair of belt pulley bases, a pair of strap pulley bases, a pair of cord segments, and elastic strapping, wherein each belt pulley base is connected to one of the pair of strap pulley bases via a cord segment, and wherein the elastic strapping elastically couples the pair of strap pulley bases together;

a pair of belt arms, wherein each belt arm is configured to couple to one of the pair of belt pulley bases and extend outwardly from the tightening mechanism; and a pair of tightening straps, wherein each tightening strap is configured to couple with a distal end of a respective one of the pair of belt arms and further configured to couple with the tightening mechanism.

2. The orthotic brace of claim 1, wherein the distal ends of each of the pair of belt arms are configured to couple together thereby securing the orthotic brace to a body of a wearer.

3. The orthotic brace of claim 1, wherein the tightening mechanism further includes a pair of strap fasteners that are each coupled to one of the pair of cord segments.

4. The orthotic brace of claim 3, wherein each of the pair of tightening straps is configured to be threaded through one of the pair of strap fasteners and coupled to itself.

5. The orthotic brace of claim 4, wherein pulling of the pair of tightening straps in opposite directions away from the tightening mechanism activates a respective one of the pair of cord segments thereby reducing a distance between each of the pair of belt pulley bases and a corresponding one of the pair of strap pulley bases.

6. The orthotic brace of claim 1, wherein the tightening mechanism includes a set of first side components and a set of second side components, wherein the set of first side components includes a first belt pulley base of the pair of belt pulley bases, a first strap pulley base of the pair of strap pulley bases, and a first cord segment of the pair of cord segments, wherein the set of second side components includes a second belt pulley base of the pair of belt pulley bases, a second strap pulley base of the pair of strap pulley bases, and a second cord segment of the pair of cord segments, and where the set of first side components and the set of second side components are elastically coupled together via the elastic strapping.

7. The orthotic brace of claim 6, wherein a first tightening strap is coupled to the set of first side components via a first strap fastener, and wherein pulling the first tightening strap in a distal direction opposite the tightening mechanism results in the first strap fastener and a portion of the first cord segment in the distal direction thereby reducing a distance between the first belt pulley base and the first strap pulley base.

8. The orthotic brace of claim 7, wherein a second tightening strap is coupled to the set of second side components via a second strap fastener, and wherein pulling the second tightening strap in a distal direction opposite the tightening mechanism results in the second strap fastener and a portion of the second cord segment in the distal direction thereby reducing a distance between the second belt pulley base and the second strap pulley base.

9. The orthotic brace of claim 1, wherein the each of the pair of cord segments extends between one of the pair of belt pulley bases and a corresponding strap pulley base in a back-and-forth manner.

10. The orthotic brace of claim 1, wherein each of the pair of belt arms includes a pocket at the distal end, wherein a first tightening strap of the pair of tightening straps extends from the pocket of a first belt arm of the pair of belt arms, and wherein a second tightening strap of the pair of tightening straps extends from the pocket of a second belt arm of the pair of belt arms.

11. The orthotic brace of claim 1, wherein the tightening mechanism is disposed within a posterior sleeve and configured to placement on a backside of a wearer.

12. The orthotic brace of claim 11, wherein the posterior sleeve includes a pocket that is configured to receive a thermal therapy pack.

13. The orthotic brace of claim 11, wherein the tightening mechanism is removably coupled to the posterior sleeve.

14. The orthotic brace of claim 1, wherein an upper side of each of the pair of belt arms includes a tapered portion.

15. The orthotic brace of claim 1, wherein each side of the tightening mechanism is configured to be adjusted individually through a respective tightening strap, and wherein the elastic strapping coupling the pair of strap pulley bases together provides flexibility and elasticity to the tightening mechanism upon adjustment of either or both sides of the tightening mechanism.

16. An orthotic brace comprising:

a tightening mechanism including a pair of belt pulley bases and at least a first cord segment, wherein the pair of belt pulley bases includes a first belt pulley base and a second belt pulley base;

a pair of belt arms, wherein each belt arm is configured to couple to one of the pair of belt pulley bases and extend outwardly from the tightening mechanism, wherein distal ends of each of the pair of belt arms are configured to couple together thereby securing the orthotic brace to a body of a wearer; and a pair of tightening straps, wherein each tightening strap is configured to couple with the distal end of a respective one of the pair of belt arms and further configured to couple with the tightening mechanism.

17. The orthotic brace of claim 16, wherein the tightening mechanism includes the pair of belt pulley bases, a pair of strap pulley bases including a first strap pulley base and a second strap pulley base, a pair of cord segments including the first cord segment and a second cord segment, and elastic strapping, wherein each belt pulley base of the pair of belt pulley bases is connected to one of the pair of strap pulley bases via either the first cord segment or the second cord segment, and wherein the elastic strapping elastically couples the pair of strap pulley bases together.

18. The orthotic brace of claim 17, wherein the tightening mechanism further includes a pair of strap fasteners that are each coupled to one of the pair of cord segments.

19. The orthotic brace of claim 16, wherein the first cord segment is interchanged between a first set of pulleys located in lower regions of the first strap pulley base and the first belt pulley base.

20. The orthotic brace of claim 19, wherein the tightening mechanism includes a second cord segment that is interchanged between a second set of pulleys located in upper regions of the first-second strap pulley base and the second belt pulley base.

* * * * *